(12) United States Patent
Azure

(10) Patent No.: US 8,880,195 B2
(45) Date of Patent: Nov. 4, 2014

(54) TRANSURETHRAL SYSTEMS AND METHODS FOR ABLATION TREATMENT OF PROSTATE TISSUE

(75) Inventor: Larry Azure, LaConner, WA (US)

(73) Assignee: LaZure Technologies, LLC, LaConner, WA (US)

( * ) Notice: Subject to any disclaimer, the term of this patent is extended or adjusted under 35 U.S.C. 154(b) by 1361 days.

(21) Appl. No.: 12/283,940

(22) Filed: Sep. 15, 2008

(65) Prior Publication Data

US 2009/0076494 A1   Mar. 19, 2009

Related U.S. Application Data

(60) Provisional application No. 60/972,698, filed on Sep. 14, 2007.

(51) Int. Cl.
| | | |
|---|---|---|
| A61N 1/00 | (2006.01) | |
| A61B 18/04 | (2006.01) | |
| A61B 18/14 | (2006.01) | |
| A61B 18/00 | (2006.01) | |
| A61B 17/00 | (2006.01) | |

(52) U.S. Cl.
CPC ... *A61B 18/1485* (2013.01); *A61B 2018/00547* (2013.01); *A61B 18/1492* (2013.01); *A61B 2018/1425* (2013.01); *A61B 2017/00274* (2013.01); *A61B 2018/00577* (2013.01); *A61B 18/1477* (2013.01); *A61B 2018/00285* (2013.01); *A61B 2018/0022* (2013.01); *A61B 2018/00214* (2013.01)
USPC .............................. 607/143; 607/148; 606/34

(58) Field of Classification Search
USPC .......... 606/32, 34, 41–44; 607/115, 116, 143, 607/148
See application file for complete search history.

(56) References Cited

U.S. PATENT DOCUMENTS

| | | |
|---|---|---|
| 3,991,770 A | 11/1976 | LeVeen |
| 4,016,886 A | 4/1977 | Doss et al. |
| 4,346,715 A | 8/1982 | Gammell |
| 4,448,198 A | 5/1984 | Turner |
| 4,676,258 A | 6/1987 | Inokuchi et al. |
| 4,732,161 A | 3/1988 | Azam et al. |
| 4,763,671 A | 8/1988 | Goffinet |
| 4,821,725 A | 4/1989 | Azam et al. |
| 4,860,752 A | 8/1989 | Turner |

(Continued)

FOREIGN PATENT DOCUMENTS

WO    WO 2005/115535 A2    12/2005

OTHER PUBLICATIONS

Aoyagi et al., "Effects of Moderate Hyperthermia on the Rabbit Sacroma Model," *Neurol. Med. Chir. (Tokyo)* 43:105-111 (2003).

(Continued)

*Primary Examiner* — Nathan R Price
(74) *Attorney, Agent, or Firm* — Wilson Sonsini Goodrich & Rosati

(57) ABSTRACT

Transurethral systems and methods for delivering electrical energy and controlled, mild heating to a prostate tissue of a patient for destruction of cancerous and/or hyperplastic tissue. A method includes positioning an elongate urethral probe having an expandable member with electrode elements at a target location in the patient's urethra, and inflating or expanding at the target location. Secondary electrodes are positioned within or adjacent to the prostate tissue and spaced from the electrode elements of the expandable member, and an alternating electrical current flow is established between the electrode elements of the expandable member and the one or more secondary electrodes. Current delivery can be selected so as to destroy or ablate cancerous cells of the prostate tissue.

21 Claims, 11 Drawing Sheets

(56) References Cited

U.S. PATENT DOCUMENTS

| | | |
|---|---|---|
| 5,277,201 A | 1/1994 | Stern |
| 5,366,490 A | 11/1994 | Edwards et al. |
| 5,370,677 A | 12/1994 | Rudie et al. |
| 5,472,441 A | 12/1995 | Edwards et al. |
| 5,529,574 A | 6/1996 | Frackelton |
| 5,630,426 A | 5/1997 | Eggers et al. |
| 5,681,282 A | 10/1997 | Eggers et al. |
| 5,807,395 A | 9/1998 | Mulier et al. |
| 5,810,804 A | 9/1998 | Gough et al. |
| 5,827,276 A | 10/1998 | LeVeen et al. |
| 5,855,576 A | 1/1999 | Leveen et al. |
| 5,868,740 A | 2/1999 | LeVeen et al. |
| 5,935,123 A | 8/1999 | Edwards et al. |
| 5,957,922 A | 9/1999 | Imran |
| 5,968,041 A | 10/1999 | Edwards |
| 6,050,992 A | 4/2000 | Nichols |
| 6,071,280 A | 6/2000 | Edwards et al. |
| 6,090,105 A | 7/2000 | Zepeda et al. |
| 6,136,020 A | 10/2000 | Faour |
| 6,148,236 A | 11/2000 | Dann |
| 6,149,620 A | 11/2000 | Baker et al. |
| 6,212,433 B1 | 4/2001 | Behl |
| 6,231,570 B1 | 5/2001 | Tu et al. |
| 6,402,742 B1 | 6/2002 | Blewett et al. |
| 6,419,653 B2 | 7/2002 | Edwards et al. |
| 6,440,127 B2 | 8/2002 | McGovern et al. |
| 6,477,426 B1 | 11/2002 | Fenn et al. |
| 6,517,534 B1 | 2/2003 | McGovern et al. |
| 6,537,272 B2 | 3/2003 | Christopherson et al. |
| 6,682,555 B2 | 1/2004 | Cioanta et al. |
| 6,738,663 B2 | 5/2004 | Schroeppel et al. |
| 6,743,226 B2 | 6/2004 | Cosman et al. |
| 6,850,804 B2 | 2/2005 | Eggers et al. |
| 6,853,864 B2 | 2/2005 | Litovitz |
| 6,866,624 B2 | 3/2005 | Chornenky et al. |
| 6,868,289 B2 | 3/2005 | Palti |
| 6,939,346 B2 | 9/2005 | Kannenberg et al. |
| 6,944,504 B1 | 9/2005 | Arndt et al. |
| 6,958,064 B2 | 10/2005 | Rioux et al. |
| 6,993,394 B2 | 1/2006 | Eggers et al. |
| 6,994,706 B2 | 2/2006 | Chornenky et al. |
| 7,016,725 B2 | 3/2006 | Palti |
| 7,053,063 B2 | 5/2006 | Rubinsky et al. |
| 7,089,054 B2 | 8/2006 | Palti |
| 7,135,029 B2 | 11/2006 | Makin et al. |
| 7,136,699 B2 | 11/2006 | Palti |
| 7,146,210 B2 | 12/2006 | Palti |
| 7,238,182 B2 | 7/2007 | Swoyer et al. |
| 7,311,708 B2 | 12/2007 | McClurken |
| 7,333,852 B2 | 2/2008 | Palti |
| 7,680,543 B2 | 3/2010 | Azure |
| 7,722,606 B2 | 5/2010 | Azure |
| 2002/0058933 A1 | 5/2002 | Christopherson et al. |
| 2002/0077676 A1 | 6/2002 | Schroeppel et al. |
| 2002/0082610 A1 | 6/2002 | Cioanta et al. |
| 2003/0060856 A1 | 3/2003 | Chornenky et al. |
| 2003/0069619 A1 | 4/2003 | Fenn et al. |
| 2003/0130575 A1 | 7/2003 | Desai |
| 2003/0150372 A1 | 8/2003 | Palti |
| 2003/0225403 A1 | 12/2003 | Woloszko et al. |
| 2004/0068297 A1 | 4/2004 | Palti |
| 2004/0087939 A1 | 5/2004 | Eggers et al. |
| 2004/0116952 A1 | 6/2004 | Sakurai et al. |
| 2004/0176804 A1 | 9/2004 | Palti |
| 2004/0215179 A1 | 10/2004 | Swoyer et al. |
| 2004/0230190 A1 | 11/2004 | Dahla et al. |
| 2005/0090732 A1 | 4/2005 | Ivkov et al. |
| 2005/0171523 A1 | 8/2005 | Rubinsky et al. |
| 2005/0171574 A1 | 8/2005 | Rubinsky et al. |
| 2005/0209640 A1 | 9/2005 | Palti |
| 2005/0209641 A1 | 9/2005 | Palti |
| 2005/0209642 A1 | 9/2005 | Palti |
| 2005/0222623 A1 | 10/2005 | Kroll et al. |
| 2005/0222646 A1 | 10/2005 | Kroll et al. |
| 2005/0240173 A1 | 10/2005 | Palti |
| 2005/0240228 A1 | 10/2005 | Palti |
| 2005/0251126 A1 | 11/2005 | Gellman et al. |
| 2006/0079883 A1 | 4/2006 | Elmouelhi et al. |
| 2006/0118127 A1 | 6/2006 | Chinn |
| 2006/0149226 A1 | 7/2006 | McCullagh et al. |
| 2006/0149341 A1 | 7/2006 | Palti |
| 2006/0155270 A1 | 7/2006 | Hancock et al. |
| 2006/0167499 A1 | 7/2006 | Palti |
| 2006/0217694 A1 | 9/2006 | Chin et al. |
| 2006/0217703 A1 | 9/2006 | Chornenky et al. |
| 2006/0233867 A1 | 10/2006 | Palti |
| 2006/0237019 A1 | 10/2006 | Palti |
| 2006/0241547 A1 | 10/2006 | Palti |
| 2006/0241577 A1 | 10/2006 | Balbierz et al. |
| 2006/0282122 A1 | 12/2006 | Palti |
| 2006/0293713 A1 | 12/2006 | Rubinsky et al. |
| 2007/0135879 A1 | 6/2007 | McIntyre et al. |
| 2007/0225766 A1 | 9/2007 | Palti |
| 2008/0033422 A1 | 2/2008 | Turner et al. |
| 2009/0076496 A1 | 3/2009 | Azure |
| 2009/0076502 A1 | 3/2009 | Azure |

OTHER PUBLICATIONS

Baronzio and Hager, "Medical Intelligence Unit—Hyperthermia in Cancer Treatment: A Primer," Landes Bioscience and Springer Science+Business Media LLC; ISBN:0-387-33440-8 (2006).

Chan et al., "Electrically Stimulated Cell Membrane Breakdown in Human Placenta TL and Lung Cancer Cell A549 in 3D Trap Arrays on Si Substrate," *Device Research Conference*, pp. 103-104 (Jun. 23-25, 2003).

Chang, D.C., "Design of protocols for electroporation and electrofusion: Selection of electrical parameters," in D. C. Chang, B. M. Chassy, J. A. Saunders and A. E. Sowers. (Ed.Eds.), *Guide to Electroporation and Electrofusion*. Academic Press, Inc., San Diego, pp. 429-455 (1992).

Chang, D.C., "Structure and dynamics of electric field-induced membrane pores as revealed by rapid-freezing electron microscopy," in D. C. Chang, B. M. Chassy, J. A. Saunders and A. E. Sowers. (Ed.Eds.), *Guide to Electroporation and Electrofusion*. Academic Press, Inc., San Diego, pp. 9-27 (1992).

Coss et al., "Effects of Hypothermia (41.5°) on Chinese Hamster Ovary Cells Analyzed in Mitosis," *Cancer Research* 39:1911-1918 (1979).

Cucullo et al., "Very Low Intensity Alternating Current Decreases Cell Proliferation," *GLIA* 51:65-72 (2005).

DeFord et al., "Effective Estimation and Computer Ccontrol of Minimum Tumour Temperature During Conductive Interstitial Hyperthermia," *Int. J. Hyperthermia* 7:441-453 (1991).

Haemmerich et al., "RF Ablation at Audio Frequencies Preferentially Targets Tumor—a Finite Element Study," *Proceedings of the Second Joint EMBS/BMES Conf.*, pp. 1797-1798 (Oct. 23-26, 2002).

Haemmerich and Wood, "Hepatic Radiofrequency Ablation at Low Frequencies Preferentially," *Int. J. Hyperthermia* 22:563-574 (2006).

Janigro et al., "Alternating Current Electrical Stimulation Enhanced Chemotherapy: a Novel Strategy to Bypass Multidrug Resistance in Tumor Cells," *BMC Cancer* 6:1-12 (2006).

Kirson et al., "Disruption of Cancer Cell Replicatioin by Alternating Electric Fields," *Cancer Res.* 64:3288-3295 (2004).

Kirson et al., "Alternating Electric Fields Arrest Cell Proliferation in Animal Tumor Models and Human Brain Tumors," *PNAS* 104:10152-10157 (2007).

Marmor et al., "Tumor Cure and Cell Survival After Localized Radiofrequency Heating," *Cancer Research* 37:879-883 (1977).

Miller et al., "Cancer Cells Ablation With Irreversible Electroporation," *Technology in Cancer Research & Treatment* 4:1-7 (2005).

Oleson et al., "Biological and Clinical Aspects of Hyperthermia in Cancer Therapy," *Am J. Clin. Oncol.* 11:368-380 (1988).

Pethig, R., "Dielectric Properties of Biological Materials: Biophysical and Medical Applications," *IEEE Trans. EI* 19(5): 453-473 (1984).

Proskuryakov et al., "Necrosis is an Active and Controlled Form of Programmed Cell Death," *Biochemistry (Moscow)* 67:387-408 (2002).

(56) References Cited

OTHER PUBLICATIONS

Rubinsky et al., "Irreversible Electroporation: a New Ablation Modality—Clinical Implications," *Tech. Cancer Res. Treatment* 6:1-12 (2007).

Shimm and Gerner, "Hyperthermia in the Treatment of Malignancies," in: Lehman, Justus F., *Therapeutic Heat and Cold* (Maryland, Williams & Wilkins), Ch. 14, pp. 674-699. ISBN 0-683-04908-9 (1990).

Stix, "Blockbuster—New Understanding of the Biology Behind a Successful Cancer Therapy May Lead to a Drug That Can Treat an Array of Solid Tumors," *Scientific American*, pp. 60-63 (May 2006).

Tello et al., "Electrochemical Therapy to Treat Cancer (In Vivo Treatment)," *Proceedings of the 20th Annual International Conference of the IEEE EMBS*, pp. 3524-3527 (Aug. 23-26, 2007).

Yi, "Cellular Ion Content Changes During and After Hyperthermia," *Biochem. Biophys. Res. Communic.* 91:177-182 (1979).

Zimmermann, U., "Electric field-mediated fusion and related electrical phenomena," *Biochim Biophys Acta* 694(3): 227-277 (1982).

Zimmermann, U., et al. "Transcellular ion flow in *Escherichia coli* B and electrical sizing of bacterias," *Biophys. J.* 13(10): 1005-1013 (1973).

Zimmermann, U., et al., "Rotation of cells in an alternating electric field: the occurrence of a resonance frequency," *Z. Naturforsch* [C] 36(1-2): 173-177 (1981).

European search report dated Nov. 23, 2012 for EP Application No. 08830923.2.

International search report and written opinion dated Nov. 17, 2008 for PCT/US2008/076470.

International search report and written opinion dated Nov. 18, 2008 for PCT/US2008/076465.

International search report and written opinion dated Nov. 18, 2008 for PCT/US2008/076471.

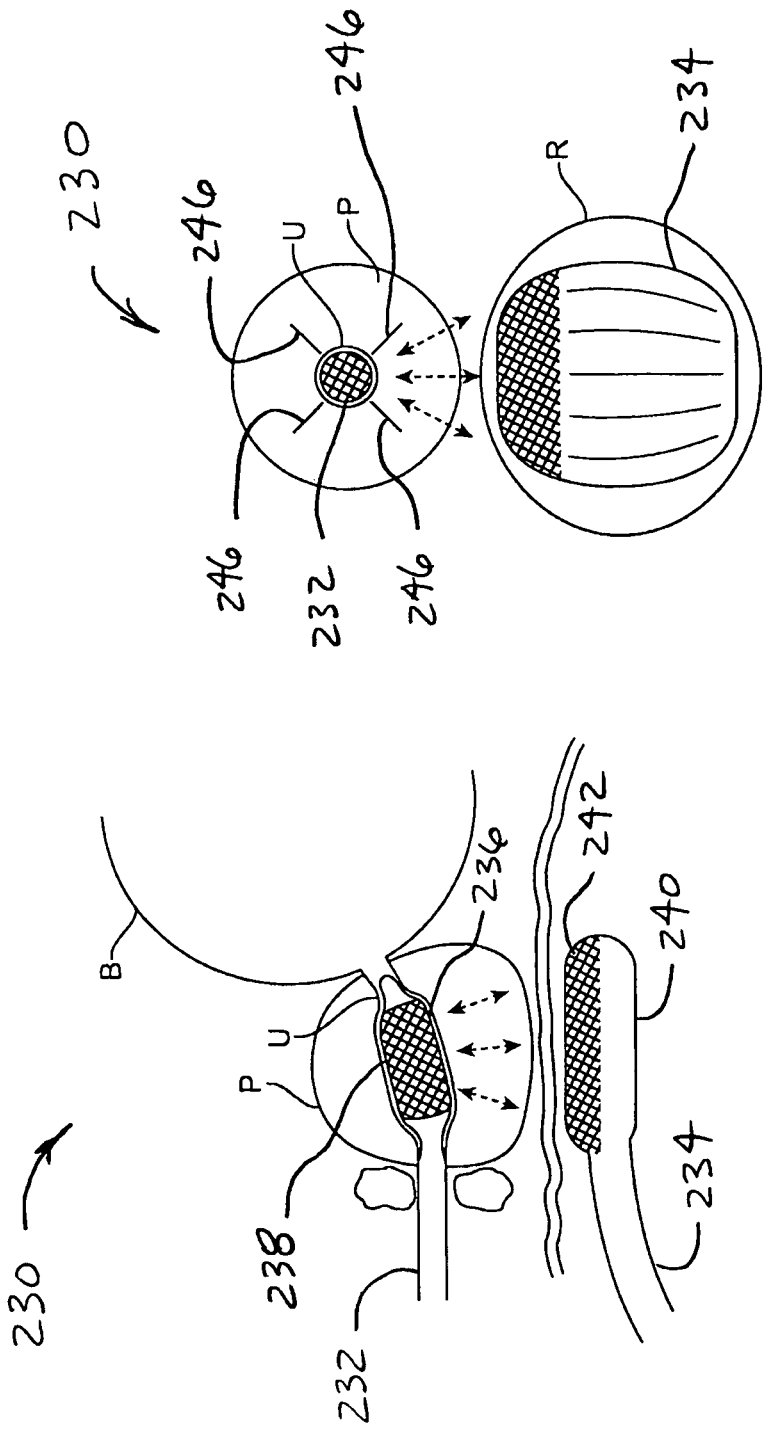

TRANSURETHRAL SYSTEMS AND METHODS FOR ABLATION TREATMENT OF PROSTATE TISSUE

CROSS-REFERENCES TO RELATED APPLICATIONS

This application claims the benefit under 35 U.S.C. §119 (e) of U.S. Provisional Patent Application No. 60/972,698, filed Sep. 14, 2007, the full disclosure of which is incorporated herein by reference.

BACKGROUND OF THE INVENTION

The present invention relates generally to electric field delivery to a prostate tissue of a patient. More particularly, the present invention provides transurethral systems and methods for delivering electrical energy and controlled, mild heating to a prostate tissue of a patient for destruction of cancerous and/or hyperplastic tissue.

The prostate gland is a walnut-sized gland located in the pelvic area, just below the outlet of the bladder and in front of the rectum. It encircles the upper part of the urethra, which is the tube that empties urine from the bladder. The prostate is an important part of the male reproductive system, requiring male hormones like testosterone to function properly, and helps to regulate bladder control and normal sexual functioning. The main function of the prostate gland is to store and produce seminal fluid, a milky liquid that provides nourishment to sperm, and increases sperm survival and mobility.

Cancer of the prostate is characterized by the formation of malignant (cancerous) cells in the prostate. Prostate cancer is the leading cancer related cause of death in men in the United States. There are currently over 2 million men in the United States with prostate cancer, and it is expected that there will be approximately 190,000 new cases of prostate cancer diagnosed, with 28,000 men dying from the disease in 2008.

In addition to risks of morbidity due to prostate cancer, most men over 60 years old experience partial or complete urinary obstruction due to enlargement of the prostate. This condition can originate from prostate cancer, or more typically, from benign prostatic hyperplasia (BPH), which is characterized by an increase in prostate size and tissue mass near the urethra.

Common active treatment options include surgery and radiation. Surgery often includes the complete surgical removal of the prostate gland ("Radical Prostatectomy"), and in certain instances the regional lymph nodes, in order to remove the diseased tissue from the body. In some instances, a nerve sparing prostatectomy is attempted in an effort to maintain erectile function in the patient after treatment. Side effects associated with radical prostatectomy can include pain, inflammation, infection, incontinence, shorter penis and impotence.

Radiation therapy is another treatment option for prostate cancer and is characterized by the application of ionizing radiation to the diseased area of the prostate. Ionizing radiation has the effect of damaging a cells DNA and limiting its ability to reproduce. For Prostate Cancer treatment, two methods of radiation therapy include External Beam Radiation Therapy (EBRT) and internal radiation, commonly known as Brachytherapy. EBRT involves the use of high-powered X-rays delivered from outside the body. The procedure is painless and only takes a few minutes per treatment session, but needs to be done extended periods of five days a week, for about seven or eight weeks. During EBRT, the rays pass through and can damage other tissue on the way to the tumor, causing side effects such as short-term bowel or bladder problems, and long-term erectile dysfunction. Radiation therapy can also temporarily decrease energy levels and cause loss of appetite.

Brachytherapy involves the injection of tiny radioactive isotope containing 'seeds' into the prostate. Once positioned in the tissue, the radiation from the seeds extends a few millimeters to deliver a higher radiation dose in a smaller area, causing non-specific damage to the surrounding tissue. The seeds are left in place permanently, and usually lose their radioactivity within a year. Internal radiation also causes side effects such as short-term bowel or bladder problems, and long-term erectile dysfunction. Internal radiation therapy can also temporarily decrease energy levels and cause loss of appetite. It is also common for the implanted seeds to migrate from the prostate into the bladder and then be expelled through the urethra during urination. Most significant, however, is the change in the texture of the prostate tissue over time, making the subsequent removal of the gland, as described above, complicated and difficult as a secondary treatment.

Given the significant side-effects with existing treatments such as radical prostatectomy and radiation therapy, less invasive and less traumatic systems and procedures have been of great interest. One such more minimally invasive system developed in recent years includes so called "Trans-urethral Needle Ablation" or TUNA, which involves passing a radiofrequency (RF) device such as a catheter probe or scope into the urethra for delivery of high frequency energy to the tissue. The RF instruments include electrode tips that are pushed out from the side of the instrument body along off-axis paths to pierce the urethral wall and pass into the prostatic tissue outside of the urethra. High-frequency energy is then delivered to cause high-temperature ionic agitation and frictional heating to tissues surrounding the electrodes. The high-temperature induced in the tissue includes induction of extremely high temperatures, often up 100 degrees C., and is generally is non-specific to cancerous tissue, destroying both healthy and non-healthy tissue.

Another technique developed in recent years for treating BPH is Trans-urethral Microwave Thermo Therapy (or "TUMT"). This technique involves use of a device having a microwave probe or antenna located near its distal end and connected to an external generator of microwave power outside the patient's body. The microwave probe is inserted into the urethra to the point of the prostate for energy delivery and microwave electromagnetic heating. Since the microwave probe delivers substantial heating that can cause unwanted damage to healthy tissues or to the urethra, devices typically make use of a cooled catheter to reduce heating immediately adjacent to the probe. The objective is to carefully balance cooling of the urethra to prevent damage to it by the heating process, while at the same time delivering high temperature heating (greater than 50 degrees C.) to the prostatic tissue outside of and at a distance from the urethra. In this procedure, the prostatic tissue immediately around the urethra and the urethra itself are deliberately spared from receiving an ablative level of heating by attempting to keep the temperatures for these structures at less than 50 degrees C. Unfortunately, controlling the tissue heating due to the applied microwave energy is difficult and unintended tissue damage can occur. Further, destruction of tissue beyond the cooled region is indiscriminate, and control of the treatment zone is imprecise and limited in the volume of tissue that can be effectively treated.

Accordingly, there is a continuing interest to develop less invasive devices and methods for the treatment of BPH and prostate cancer that is more preferential to destruction of target tissue and more precisely controllable.

BRIEF SUMMARY OF THE INVENTION

The present invention includes methods and systems for applying electric fields to prostate tissue of a patient for controllable and/or preferential cancerous cell destruction and tissue ablation. Methods and systems according to the present invention will typically include use and positioning of an elongate urethral probe that can be inserted in the urethra of the patient and advanced along the patient's urethra for positioning at a desired location. A urethral probe includes a distally positioned expandable member, such as a balloon configured for expansion in the urethra of the patient. The probe can be coupled to a controller or control unit and power source, such as coupled about a proximal portion positioned externally to the patient's body during treatment. The expandable member will include conductive electrode elements patterned or disposed on an outer surface of the expandable member. The elongated body or shaft of the probe can include an inner lumen or passage with electrical coupling members, such as insulated wires, for coupling the electrode elements of the expandable member to the proximal end and/or an externally positioned controller and/or power source. The distal portion of the urethral probe is insertable in the urethra and can be advanced through the patient's urethra so as to position the expandable member at a target location in the patient's urethra, including a portion or length of the urethra passing through the patient's prostate. Upon locating the distal portion at the target location, the balloon or expandable member can be inflated or expanded so as to position or bring the conductive electrode elements in improved or better contact with an inner surface of the patient's urethra at the target location, for energy delivery and establishing current flow in the desired manner. The electrode elements can be positioned such that applied electric fields extend or radiate throughout the target tissue region. In some embodiments, energy is applied to deliver mild and controlled heating of the tissue.

As described above, electrode elements of the expandable member of the urethral probe can be electrically coupled to a control unit and/or power source for energy delivery and establishment of the desired electric field through the target tissue or a volume of the prostate tissue to be treated. Energy delivery can include establishing an electrical current flow between the electrode elements of the expandable member and the one or more secondary electrodes positioned within or adjacent to the prostate tissue and spaced from the electrode elements of the expandable member. Current flow is established between electrode elements of the expandable member and the secondary electrodes in a bipolar arrangement for formation of a sort of current circuit, allowing the applied field to substantially be contained between the electrodes or within the volume defined by the secondary electrodes with the expandable member positioned in the defined volume. Thus, the control unit and power source can be coupled to the urethral probe and electrode elements of the expandable member, and configured for energy application and establishment of current flow through the target tissue region, including a volume of the patient's prostate tissue substantially defined by the positioned electrodes/electrode elements.

The control system and power source can be configured for delivery of various possible energy ranges including, e.g., alternating electrical current flow in the radiofrequency (RF) range. Energy application according to the present invention can be selected to establish an alternating electrical current flow through the tissue sufficient to mildly heat or deliver low levels of hyperthermia. Thus, current flow can be delivered to generate small changes/elevations in temperature in the target tissue region, with resulting hyperthermic effects typically causing average tissue temperatures of less than about 50 degrees C., and typically about 40-48 degrees C. (e.g., about 42-45 degrees C.). In one example, energy delivery will include relatively low power ablation including intermediate current frequency less than about 300 kHz, and typically about 50 kHz to about 250 kHz. Further, energy delivery, in certain embodiments, can include establishing current flow fields substantially radially throughout the target tissue and/or in a plurality of different directions. For example, energy delivery can include creating a current flow field extending radially from the an electrode or electrode elements positioned within a treatment volume, such as the electrode elements of the urethral probe expandable member positioned in the urethra of the patient. Energy delivery in the manner described herein provides numerous advantages, including precisely controlling the energy application to the target tissue, controlling thermal effects in the desired heating ranges (e.g., mild hyperthermia), and preferentially destroying cancerous cells with limited or no observable damage to healthy or non-cancerous tissues.

Thus, in one aspect, the present invention includes methods and systems for delivering an electric field to ablate or destroy cancerous cells of a prostate tissue of a patient including positioning of an elongate urethral probe comprising a proximal end and a distal portion having an expandable member, and one or more conductive electrode elements disposed on an outer surface of the expandable member. Electric field delivery includes advancing the distal portion of the probe through the patient's urethra so as to position the expandable member at a target location in the patient's urethra. Once positioned, the expandable member is inflated or expanded at the target location so as to position the conductive electrode elements in contact with an inner surface of the patient's urethra at the target location. One or more secondary electrodes are positioned within or adjacent to the prostate tissue and spaced from the electrode elements of the expandable member, and an alternating electrical current flow is established between the electrode elements of the expandable member and the one or more secondary electrodes. Current delivery can be selected so as to preferentially destroy cancerous cells of the prostate tissue.

In another aspect, systems and methods include an elongate urethral probe including a proximal end and a distal portion having an expandable member, and one or more conductive electrode elements disposed on an outer surface of the expandable member. The probe further includes one or more secondary electrodes deployable from a body of the elongate probe. A method includes advancing the distal portion of the probe through the patient's urethra so as to position the expandable member at a target location in the patient's urethra. The positioned expandable member is inflated or expanded at the target location so as to position the conductive electrode elements in contact with an inner surface of the patient's urethra at the target location. The deployable electrodes can be advanced or deployed from the body of the probe and through the urethral wall into the prostate tissue and spaced from the positioned expandable member. The deployed electrodes advanced or positioned in this manner can be positioned to substantially define an ablation volume with the expandable member positioned within the ablation volume. The method further includes establishing an electrical current flow between the electrode elements of the expandable member and the one or more secondary electrodes.

In yet another aspect, methods and systems of the present invention include an elongate urethral probe one or more individual elongated needle electrodes that can be separately, from the urethral probe, positioned in the prostate tissue or the vicinity of the prostate tissue. Elongated needle electrodes will include a distal portion that can include a sharpened distal tip and a proximal portion. A method can include advancing the distal portion of the probe through the patient's urethra so as to position the expandable member at a target location in the patient's urethra, and expanding the expandable member at the target location so as to position the conductive electrode elements in contact with an inner surface of the patient's urethra at the target location. The method further includes positioning the elongated needle electrodes within or adjacent to the prostate tissue and spaced from the electrode elements of the expandable member. The positioning can be accomplished by advancing the needle electrodes through the perineum of the patient and into the prostate tissue in the desired location. Once the urethral probe and needle electrodes are positioned, treatment includes establishing an electrical current flow between the electrode elements of the expandable member and the positioned needle electrodes.

In another aspect of the present invention, methods and systems include an elongate urethral probe having a plurality of deployable electrodes that can be advanced through the urethral wall and into the prostate tissue in a desired arrangement for energy delivery. An elongate urethral probe can include a proximal end, a distal portion, and a plurality of electrodes deployable from the distal portion. A method can include advancing the distal portion of the probe through the patient's urethra so as to position the distal portion near a target location in the patient's urethra. Once the distal portion is at the desired location, a plurality of outer or secondary electrodes can be deployed from the distal portion of the probe, through the urethral wall, and into the prostate tissue. The deployed outer or secondary electrodes can be positioned to substantially define an ablation volume in the prostate tissue. Further, an inner or central electrode can be deployed from the distal portion of the probe and through the urethral wall and into the prostate tissue such that the inner/central electrode is positioned within the ablation volume. Once the urethral probe and needle electrodes are positioned, treatment includes establishing an electrical current flow between the inner electrode and the one or more outer/secondary electrodes.

In yet another aspect, the present invention includes various systems for delivery of energy for treatment according to the methods of the present invention, including establishing electrical current flow for preferential destruction of cancerous or hyperplastic cells of a prostate tissue of a patient. In one embodiment, a system includes an elongate urethral probe comprising a proximal end and a distal portion having an expandable member, the expandable member including one or more conductive electrode elements. The system further includes a rectal probe having one or more electrode elements disposed on a surface of an expandable member. A control system including a power source is further included, the control system can be coupled to the elongate urethral probe and rectal probe and configured to provide alternating electrical current to the electrodes so as to establish a current flow through a volume of the patient's prostate tissue and between the electrode elements of the urethral probe and electrode elements of the rectal probe.

In yet another embodiment, the present invention includes methods and systems for delivering an electric field to destroy cancerous or proliferating cells of a target tissue or of a body lumen passing through a target tissue of a patient. Systems and methods include positioning of an elongate probe in a body lumen of the patient, the probe including a proximal end and a distal portion having an expandable member, and one or more conductive electrode elements disposed on an outer surface of the expandable member. The distal portion of the probe can be advanced through the patient's body lumen so as to position the expandable member at a target location in the lumen. Once positioned, the expandable member can be expanded (e.g., inflated, deployed) at the target location so as to position the conductive electrode elements into contact (e.g., improved or better contact) with an inner surface of the patient's lumen. Systems and methods further include positioning one or more secondary electrodes within or adjacent to the target tissue and spaced from the electrode elements of the expandable member, and establishing an electrical current flow between the electrode elements of the expandable member and the one or more secondary electrodes. Current flow may be selected so as to preferentially destroy cancerous cells of the target tissue, and may include application of mild tissue heating or hyperthermia. A body lumen can include any cavity or tube-like body organ or passage in a patient's body.

For a fuller understanding of the nature and advantages of the present invention, reference should be made to the ensuing detailed description and accompanying drawings. Other aspects, objects and advantages of the invention will be apparent from the drawings and detailed description that follows.

BRIEF DESCRIPTION OF THE DRAWINGS

FIGS. 8A and 8B illustrate current delivery in the prostate tissue of a patient between a transurethral probe and rectal probe, according to an embodiment of the present invention.

FIG. 10B illustrates current flow between positioned electrodes, according to an embodiment of the present invention.

DETAILED DESCRIPTION OF THE INVENTION

Figure 1:
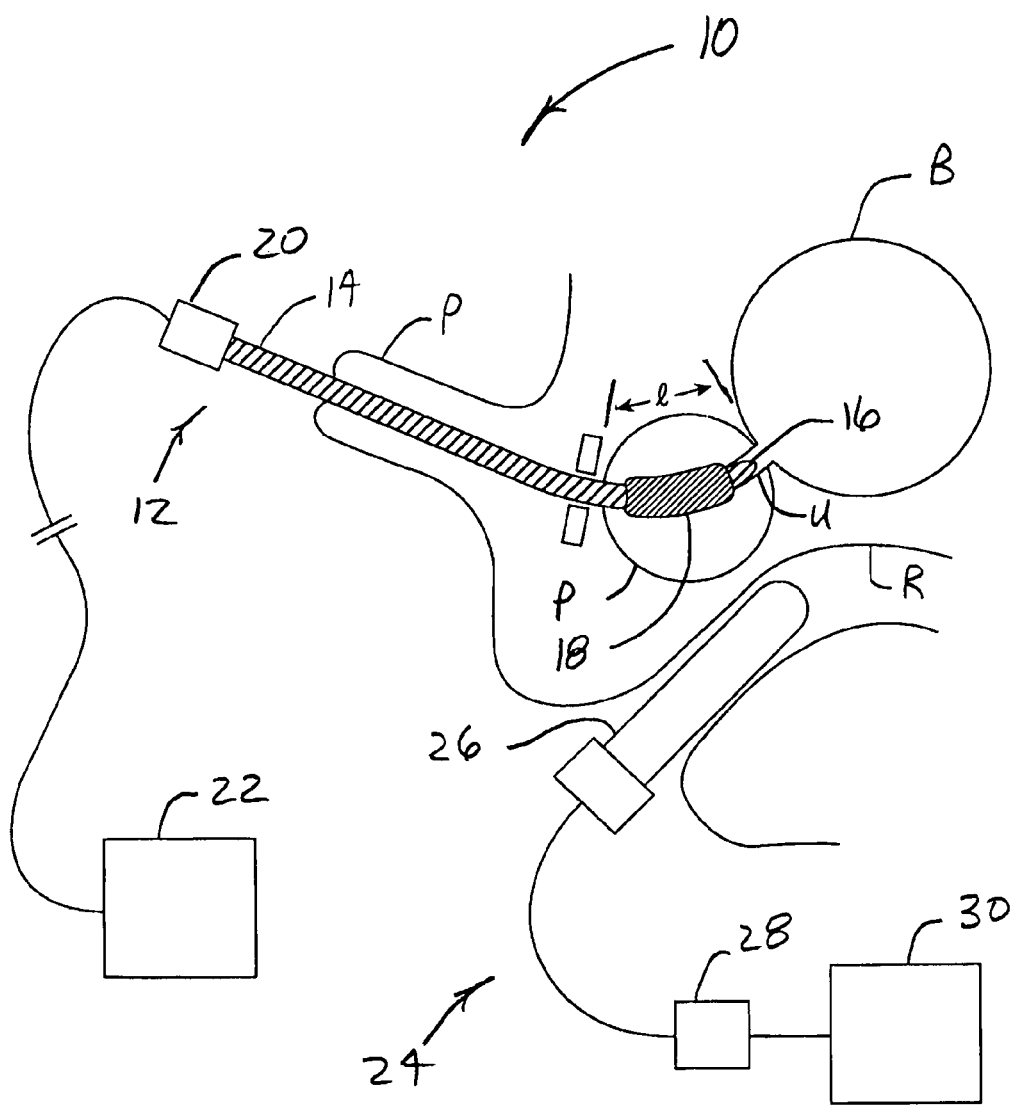
FIG. 1 illustrates a transurethral system and imaging system according to an embodiment of the present invention.

The present invention includes systems and methods for more precisely controlled energy deliver to prostate tissue for applying fields, including controlled delivery and generation of mild heating or hyperthermia to prostate tissue for the destruction of cancerous and/or treatment of hyperplastic prostate cells for treatment of benign prostatic hyperplasia (BPH).

The systems and methods described herein generally utilize an elongate urethral probe that can be inserted in the urethra of the patient and advanced along the patient's urethra for positioning at a desired location. A urethral probe can include distal expandable member or balloon configured for expansion in the urethra of the patient. The expandable member includes conductive electrode elements patterned or disposed on an outer surface of the expandable member. The distal portion of the urethral probe is inserted into the urethra and advanced to position the expandable member at a target location in the patient's urethra, and the expandable member inflated or expanded so as to bring the conductive electrode elements into improved contact with the urethral wall. Energy delivery and desired tissue heating is accomplished by establishing electrical current flow between electrodes of the expandable member and one or more electrodes (e.g., secondary electrodes) positioned in or in the vicinity of the prostate tissue and spaced from the urethral probe expandable member.

Establishment and application of energy delivery utilizing the described energy parameters and/or field delivery (e.g., orientation) can offer several advantages. First, energy delivery according to the present invention further advantageously allows a more controlled or precise therapeutic energy dose both in terms of delivery of the desired current and resulting effects, as well as more accurate delivery to the target or intended tissue. For example, current flow is established between electrodes in a bipolar arrangement, with current flow established and substantially contained between the spaced electrodes. Further, tissue heating can be more precisely controlled to prevent or minimize excessive heating and/or hot spots that can cause unintended damage to healthy or non-target tissues. For example, energy delivery can be selected (e.g., frequency ranges between about 50 kHz to about 300 kHz) such that tissue heating occurs significantly, and in some cases predominately, due to tissue resistance, rather than the high-frictional heating observed at high frequencies (e.g., 500 kHz or greater), the latter of which can include significant tissue temperature gradients throughout the treated tissue, with significant tissue temperature changes occurring through a volume of treated tissue as a function of electrode distance. While heating may occur due to both tissue resistance and frictional heating, with relative reduction of high friction type heating a more constant and controlled heating between opposing electrodes may be delivered.

Another advantage of the present inventive methods and systems is that energy delivery and application of mild hyperthermia as described has been observed to be surprisingly effective in preferentially damaging and destroying cancerous cells compared to non-cancerous or healthy cells/tissue. Preferential destruction, as described herein, refers to establishing current flow as described with application of hyperthermia, generally below about 50 degrees C., such that cytotoxic effects of treatment are, on average or as a whole, more destructive and/or lethal to cancerous or hyperplastic cells (e.g., cells exhibiting or predisposed to exhibiting unregulated growth) compared to non-cancerous or healthy cells. In some instances, establishing current flow and induction of mild hyperthermia as described herein is remarkably effective in preferentially destroying cancerous cells with limited or no observable damage to non-cancerous tissues.

Furthermore, and without being bound by any particular theory, electrode configuration and field application as described in certain embodiments (e.g., radially and/or in a plurality of different directions) may take advantage of tumor or mitotic cell physiology to increase treatment effectiveness, and can include a more optimal or effective orientation of the applied field with respect to dividing cells of the target region. For example, energy application can be accomplished such that current fields are substantially aligned at some point during energy delivery with division axes of dividing cells (e.g., cancerous cells), thereby more effectively disrupting cellular processes or mitotic events (e.g., mitotic spindle formation and the like). As cancerous cells are dividing at a higher rate compared to non-cancerous cells, field application in this manner may preferentially damage cancerous cells compared to healthy or non-dividing cells. It will be recognized, however, that energy application according to the present invention likely has several or numerous cytotoxic effects on cells of the target region and that such effects may be cumulatively or synergistically disruptive to a target cell, particularly to cells disposed or pre-disposed to unregulated growth (i.e., cancerous cells). Other cytotoxic or disruptive effects of the energy application as describe herein may occur due, for example, to application of mild hyperthermia (e.g., mild heating of tissue between about 40 to 48 degrees C.; or less than about 50 degrees C.); ion disruption, disruption of membrane stability, integrity or function; and the like.

Systems and probes of the present invention, as further described below, can include one or more expandable elements (e.g., balloon) that can be individually positioned at a target location then deployed or "inflated" to achieve improved contact with surrounding tissues (e.g., urethral wall), maximum surface area and optimal distribution of the therapeutic field. An electrically active segment of the expandable element will typically include an electrically conductive material (e.g., silver, gold, etc.) coated or deposited, e.g., on a mylar balloon. In one embodiment, prior to deployment and inflation, the expandable element can be contained inside a flexible catheter that can be guided to the treatment area. Once the delivery catheter is positioned, the "balloon" can be deployed and expanded via the circulation of fluid through the balloon, which can have a selected or controlled temperature and may act as a heat sink. The therapeutic field can than be delivered via the silver coating on the mylar balloon. Two or more probes deployed in this fashion will serve to contain the field within the treatment area.

Electrodes and probes of the present invention can be coupled to control system or control module designed to generate, deliver, monitor and control the characteristics of the applied field within the specified treatment parameters. In one embodiment, a control system includes a power source, an alternating current (AC) inverter, a signal generator, a signal amplifier, an oscilloscope, an operator interface and/or monitor and a central processing unit (CPU). The control unit can manually, automatically, or by computer programming or control, monitor, and/or display various processes and parameters of the energy application through electrodes and to the target tissue of the patient. While the control system and power source can include various possible frequency ranges, current frequency delivered to target tissue will be less than about 300 kHz, and typically about 50 kHz to about 250 kHz. Frequencies in this range have been observed as effective in precisely controlling the energy application to the target tissue, controlling thermal effects primarily to mild thermal application, and preferentially destroying cancerous cells with limited or no observable damage to non-cancerous tissues.

Energy application according to the present invention can further include mild or low levels of hyperthermia. In some embodiments, small changes/elevations in temperature in the target tissue region may occur, but will typically be no more than about 10 degrees C. above body temperature, and may be about 2 degrees to less than about 10 degrees C. above body temperature (e.g., normal human body temperature of about 38 degrees C.). Thus, local tissue temperatures (e.g., average tissue temperature in a volume of treated tissue) during treatment will typically be less than about 50 degrees C., and typically within a range of about 40-48 degrees C. In one embodiment, average target tissue temperature will be selected at about 42-45 degrees C. As target tissue temperatures rise above about 40-42 degrees C. during treatment, the cytotoxic effects of energy delivery on cancerous cells of the target region are observably enhanced, possibly due to an additive and/or synergistic effect of current field and hyperthermic effects. Where mild hyperthermic effects are substantially maintained below about 48 degrees C., the energy delivery according to the present invention appears to more preferentially destroy cancerous cells compared to healthy or non-cancerous cells of the target tissue region. Where energy delivery induces tissue heating substantially in excess of about 45-48 degrees C. (e.g., particularly above 48-50 degrees C.), the preferential cytotoxic effects on cancerous cells may begin to diminish, with more indiscriminate destruction of cancerous and non-cancerous cells occurring. Thus, a significant advantage of treatment methods according to the present invention includes the ability to precisely and accurately control energy delivery and induced hyperthermic effects, such that tissue hyperthermia can be accurately controlled and maintained in a desired temperature range(s)—e.g., temperature ranges selected for more targeted or preferential destruction of cancerous cells compared to non-cancerous cells.

Tissue temperatures can be selected or controlled in several ways. In one embodiment, tissue temperatures can be controlled based on estimated or known characteristics of the target tissue, such as tissue impedance and tissue volume, blood flow or perfusion characteristics, and the like, with energy application to the tissue selected to deliver an approximated controlled mild increase in tissue temperature. In another embodiment, tissue temperature can be actively detected or monitored, e.g., by use of a feedback unit, during treatment, with temperature measurements providing feedback control of energy delivery in order to maintain a desired target tissue temperature or range. Temperature control measures can include electronics, programming, thermosensors and the like, coupled with or included in a control unit or module of a system of the invention. Further, use of inflatable/expandable balloons and circulation heated/cooled inflation media further facilitates control and delivery of the desired treatment temperature to the target tissue.

Energy application and induction of hyperthermia in a target tissue region according to the present application can include delivery of various types of energy delivery. As described, application of generally intermediate frequency range (e.g., less than about 300 kHz) alternating current in the RF range has been observed as effective in establishing mild heating and hyperthermia, as well as current fields in a controlled manner so as to provide a cytotoxic effect, and in some instances, a preferential destructive effect to cancerous cells of a target tissue volume/region. It will be recognized, however, that additional energy applications and/or ranges may be suitable for use according to the present invention, and that systems and methods of the present invention may be amenable to use with other or additional energy applications. For example, energy application can include current flow having frequencies found generally in the RF range, as well as microwave range, including higher frequencies such as 300-500 kHz and above, and may further be amenable to use with direct current applications. Applied current can be pulsed and/or continuously applied, and energy delivery can be coupled with a feedback-type system (e.g., thermocouple positioned in the target tissue) to maintain energy application and/or tissue heating in a desired range. Methods of the present invention can include any one or more (e.g., combination) of different energy applications, induced temperatures, etc. as described herein.

In certain embodiments, particularly where energy application is selected for lower power delivery/ablation, the control system can be designed to be battery powered and is typically isolated from ground. AC current is derived from the integrated power inverter. An intermediate frequency (e.g., less than 300 kHz; or about 50 kHz to about 250 kHz) alternating current, sinusoidal waveform signal is produced from the signal generator. The signal is then amplified, in one non-limiting example to a current range of 5 mA to 50 mA and voltage of up to 20 Vrms per zone. Field characteristics including waveform, frequency, current and voltage are monitored by an integrated oscilloscope. Scope readings are displayed on the operator interface monitor. An integrated CPU monitors overall system power consumption and availability and controls the output of the signal generator and amplifier based on the treatment parameters input by the operator. The operator can define treatment parameters to include maximum voltage, maximum current or temperature, maximum power, and the like. In another embodiment, the applied field can be cycled on and off, e.g., at a high rate, to keep the temperature relatively constant and with the duty cycle (e.g., on time-off time) adjusted to accurately control temperature.

Imaging systems and devices can be included in the methods and systems of the present invention. For example, the target tissue region can be identified and/or characterized using conventional imaging methods such as ultrasound, computed tomography (CT) scanning, X-ray imaging, nuclear imaging, magnetic resonance imaging (MRI), electromagnetic imaging, and the like. In some embodiments, characteristics of the tumor, including those identified using imaging methods, can also be used in selecting ablation parameters, such as energy application as well as the shape and/or geometry of the electrodes. Additionally, these or other known imaging systems can be used for positioning and placement of the devices and/or electrodes in a patient's tissues.

As noted above, access to the target tissue or prostate tissue can be gained through the urethra of the patient. Referring to FIG. 1, a urethral access system 10 according to the present invention is illustrated. The system includes an elongated probe 12 that can be inserted in the urethra (U) of a patient via the penis (P), and advanced along the urethra (U) to the desired location within the patient's body, specifically at a target location in the prostate tissue or gland (P). The probe includes a flexible catheter having an elongated shaft 14 that can be bent or flexed while advanced into and through the urethra (U). The probe 12 includes a distal tip 16, that can be shaped (e.g., rounded) to minimize damage or trauma to the urethral wall during positioning or use. The probe 12 can optionally include a drainage lumen (not shown) that allows fluid communication between an area distal to the distal tip 16 and the exterior or a proximal portion of the probe, so as to allow draining or flushing of contents of the bladder (B) during treatment and use of the probe 12.

The urethral probe 12 includes a proximal end and a distal portion having an expandable member 18, such as a balloon configured for expansion in the urethra (U) of the patient. The proximal end 20 is positioned outside the patient's body during use, and can include a hub or handle that can be coupled to a controller or control unit 22 that can include a power source. The expandable member 18 includes conductive electrode elements patterned or disposed on an outer surface of the expandable member 18. The probe 12 will include an elongated body extending from the proximal portion of the device to the distal portion, and the elongated body can include an inner lumen or passage with electrical coupling members, such as insulated wires, for coupling the electrode elements of the expandable member 18 to the proximal end and/or an externally positioned controller and/or power source 22.

The probe 12 will be designed to include electrode elements that can be positioned in the desired location and used for delivery of electric fields to the target tissue for treatment according to the present invention. Various embodiments of electrode elements can be included in the present invention and the probe 12 can be designed or configured for delivery of electrical fields, for example, between the expandable member 18 and opposing electrode(s) (e.g., secondary electrodes) positioned in or in the vicinity of the prostate tissue (P), with current fields in some embodiments established between electrodes and typically in a plurality of directions (e.g., radially) through a volume of tissue. Electrode elements of the expandable member 18 can include conductive material deposited or patterned on a surface or at least a portion of the expandable member 18 that is brought into contact with the walls of the urethra (U) during treatment. In one embodiment, the expandable member 18 can be configured in a deployable configuration, such that the expandable member 18 may be positioned within the probe 12 shaft and then deployed from the probe 12 (e.g., from the distal end or tip of the probe) and expanded at the desired location. For example, the expandable member 18 can be positioned or disposed within in the probe 12 shaft or portion of the elongate body (e.g., shaft lumen) during advancement and positioning of the probe 12, and deployed from the probe 12 once a desired position in the patient's urethra (U) has been reached. Alternatively, in another embodiment, the expandable member 18 or balloon (e.g., electrode patterned balloon) can be coupled and positioned along the length of the probe 12 on an outer surface, with inflation or expansion of the expandable member 18 controlled by an external pressure source coupled to the proximal portion of the probe.

As indicated in FIG. 1, the urethra (U) of the patient will include a length (l) passing through the prostate tissue (P) until reaching the bladder (B). The expandable member 18 of the probe 12 can include various shapes and configurations selected to span any portion of the length (l). The expandable member 18 can be configured to span the entire length (l) (or more) or may be sized to span less than the entire portion. The expandable member 18 may be positioned at any portion along the length (l) during treatment, as well as elsewhere along the patient's urethra (U), including portions at or adjacent to locations where the urethra enters or exits the prostate tissue (P) area.

A probe 12 may include one or more electrodes (e.g., secondary electrodes) that can be positioned within the probe 12 and deployed from the probe 12 and into the prostate tissue (P). For example, such secondary electrodes can be positioned in the probe shaft 14 or body during advancement and positioning of the probe 12, and deployed from the probe 12 once a desired position has been reached. Deployable probes 12 can include needle-like electrodes, which can include a shape memory metal and configured to assume a desired shape when deployed, e.g., as discussed further below.

During use, field delivery can occur with current flow between an electrode elements of the urethral probe 12 and electrode(s) spaced from the urethral probe 12, such as electrodes positioned in the prostate tissue (P) or in the rectal area (R). As above, electrode elements, including electrodes of the expandable member 18, will be connected to an external power source or power unit (e.g., power source of control system or unit) 22, which will include a means of generating electrical power for operation of the system and probe 12, and application of electrical current to the target tissue as described herein. The power unit can include or be operably coupled to additional components, such as a control unit, driver unit, user interface, and the like (see, e.g., infra).

System 10 further includes an imaging device 24, such as an ultrasonic imaging probe, for providing images of tissues for example during positioning and/or use of the probe 12. The device 24 includes a distal imaging portion 26 including electronics and imaging components (e.g., ultrasonic scanning transducer), which can be inserted in the patient's rectum (R) and positioned against the rectal wall near the prostate (P). Imaging device 24 can include those commonly used for diagnostic medicine, such as commercially available ultrasonic imaging devices including devices similar to or as provided by Accuson, Inc. (Mountain View, Calif.). The imaging portion 26 can scan a region of the tissue to generate an image of the tissue, rectal wall (R), prostate (P), urethra (U), and/or the probe 12 located in the patient's urethra (U). The imaging device 24 can be connected to an image processing unit 28 and a display unit 30, as is common practice. In use, the display 30 provides images (e.g., real-time ultrasonic images) of the prostate (P) with the position of the probe 12 relative to the prostate (P) and target area, the bladder (B), etc. to help guide or confirm positioning of the probe 12 within the prostate (P) prior to delivery of treatment energy.

As discussed above, a probe 12 of a system, e.g., as illustrated in FIG. 1, will include electrode element patterned or otherwise disposed on an expandable member 18 or balloon disposed on a distal portion of the probe. A probe 12 can include a catheter probe having a shaft and a distally positioned balloon member having electrode elements disposed (e.g., deposited, patterned, etc.) thereon. The balloon can be coupled to one or more fluid sources positioned externally, as well as a pressure source and/or controller for inflation and deflation of the balloon. In one embodiment, the balloon can be configured such that a fluid can be circulated through the balloon and may be utilized to further effect or control temperature of tissues proximate to the balloon. The probe 12 further includes a proximal hub 20 that can include one or more electrical connections for coupling the electrode elements to an external power source and/or control unit 22, as well as fluid connections for fluidic access and control of balloon actuation and inflation, as well as circulation of fluid (e.g., cooling fluid) through the balloon. In an embodiment where the probe 12 further includes one or more deployable electrodes, actuation and positioning of such deployable electrodes can be controlled from the proximal end 20 of the probe 12, such as through the hub. In other embodiments, current flow can extend between electrode elements of the expandable member 18 positioned in the patient's urethra (U) and one or more electrode elements (e.g., secondary electrodes) spaced from the positioned expandable member 18, and may be separate from the urethral probe 12, and positioned on an opposing side of the urethral wall. For example, needle electrodes can be separately advanced through the perineum of the patient and positioned within the prostate tissue (P) around the urethra (U), with energy delivery establishing current flow between electrode elements of the urethral probe 12 and needle electrodes positioned in the prostate tissue (P). In yet another embodiment, electrode elements (e.g., electrodes disposed on an expandable balloon 18) can be positioned in the rectal cavity adjacent to the rectal wall (R), with current flow established between electrode elements of the urethral probe 12 and electrode elements of the rectally positioned device. Exemplary embodiments of system configurations and electrode positioning are discussed further below.

Figure 2:
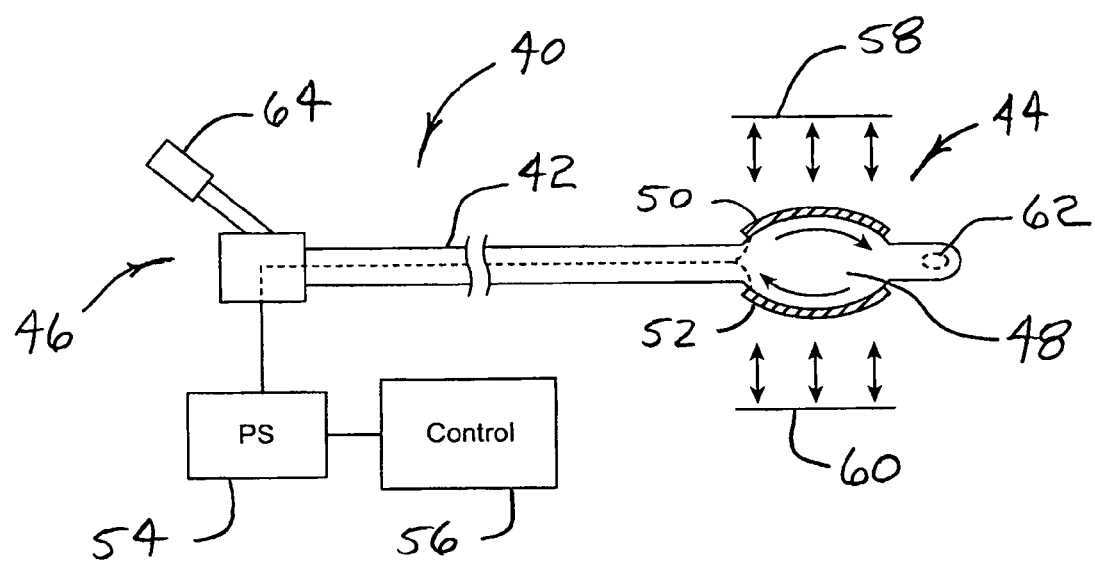
FIG. 2 illustrates a system including transurethral ablation probe coupled with a power supply and control unit, according to an embodiment of the present invention.

Referring to FIG. 2, a urethral probe 40 according to the present invention is described. The probe 40 includes a flexible elongate shaft or body 42, including a distal portion 44 and a proximal portion 46. The distal portion 44 includes an expandable balloon 48 or expandable member having electrode elements 50, 52 disposed thereon. The electrode elements 50, 52 may be electrically conductive and will include flexible or expandable materials or configurations that can be expanded with the expansion of the expandable member 48 and, when positioned in the urethra of a patient, electrode elements 50, 52 can be brought into improved contact with the urethral wall. The electrode elements 50, 52 can be connected to an external power source 54 and control unit 56 for energy delivery and establishing electric current fields between the electrode elements 50, 52 of the expandable member 48 and one or more electrodes 58, 60 (e.g., secondary electrodes) spaced from the expandable member 48. Secondary electrodes 58, 60 may be integrated or physically connected to the probe 40 (e.g., deployable therefrom) or can be separate and independently positionable, and may at least partially define a separate electrode device (see, e.g., secondary electrode embodiments discussed further below). Secondary electrodes 58, 60 may be electrically connected to the power source 54 and control unit 56. In some instances, current flow can be established between secondary electrodes 58, 60.

The distal expandable member 48 can be inflated with an inflation media (e.g., air, fluid, etc.) from an external source, and upon inflation, can provide improved contact of the electrode elements 50, 52 of the expandable member 48 with the urethral wall. The distal expandable member 48 can be connected with an external inflation source about an inflation hub positioned at the proximal portion 46 of the probe 40. Inflation media can be flowed into the expandable member 48 to obtain a desired pressure within the expandable member 48 for member expansion, and may be further circulated at a desired inflation pressure through the expansion member 48, as indicated by the directional arrows shown on the expandable member 48 in FIG. 2. In one embodiment, the inflation media can be heated or cooled to a desired temperature, e.g., by heating or cooling at an external location, and circulated through the expandable member 48 to further control tissue temperature at the treatment location, either by delivering additional heating or cooling energy, and/or by acting as a sort of heat sink to maintain local tissue temperature at a substantially constant or desired temperature range.

The probe 40 can further include an opening or port 62 at the distal portion 44 of the probe 40, with the port coupled 62 with a channel or lumen passing through the elongate shaft 42 and to the externally positioned hub 64, and may provide fluid communication to a location distal to the probe (e.g., distal the distal tip of the probe 40), such as drainage or infusion of fluids to a location distal to the probe 40 (e.g., the patient's bladder). While the probe 40 is illustrated in FIG. 2 as having a single expandable member 48, it will be understood that this and other designs/configurations of the probe 40 may optionally further include one or more additional expandable members 48 or balloons. For example, the probe 40 may include a Foley-type catheter design, where the probe includes a second balloon located on the probe 40 body distal to the expandable member 48 for positioning and/or anchoring in the patient's bladder during use of the probe or treatment (see, e.g., FIG. 9).

Figure 3A:
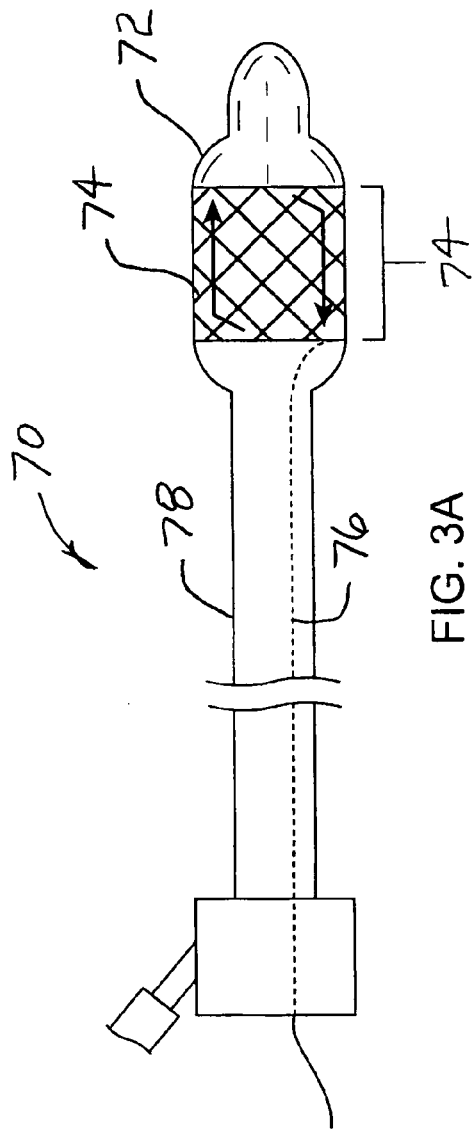
FIGS. 3A and 3B illustrate elongate transurethral probes according to various embodiments of the present invention.
Figure 3B:
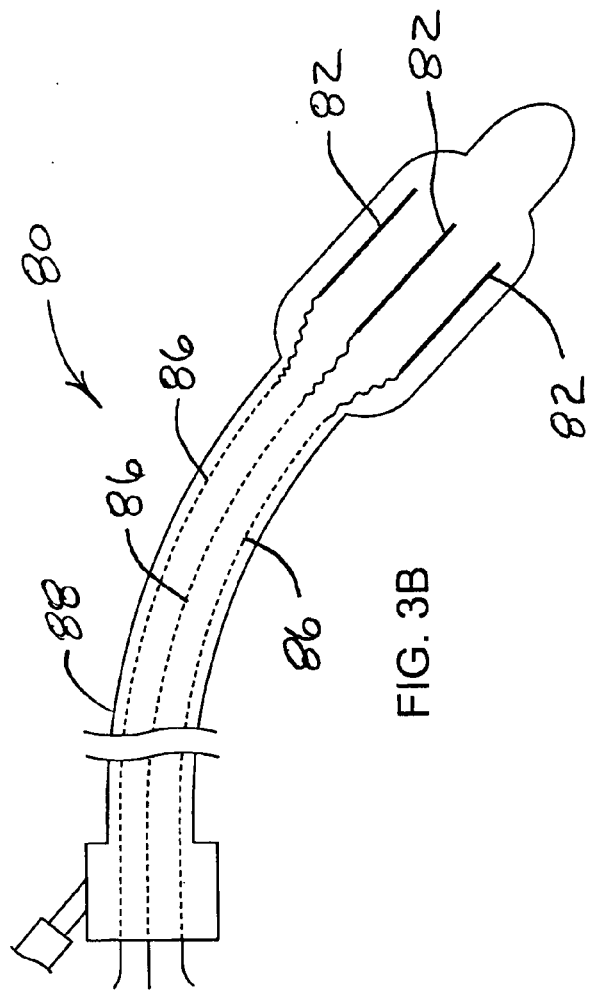

As described above, a urethral probe 40 of the present invention will include a distal portion 44 having an expandable member 48 including one or more electrode elements 50, 52 that can be brought into contact with the patient's urethral wall at a desired location. The electrode elements 50, 52 may be electrically conductive, exposed electrode coating, sheets, wires, films, braids, flexible materials, and the like that can be expanded with the expansion of the expandable member 48 and, when positioned in the urethra of a patient, electrode elements 50, 52 can be brought into improved contact with the urethral wall. The electrode elements 50, 52 may be patterned, disposed, or spaced on the expandable member 48 in various configurations and designs to suit clinical or treatment needs. In one embodiment, electrode elements 50, 52 can include a somewhat uniform coating that may partially or entirely coat or cover the surface of an expandable member 48. FIG. 3A illustrates a probe 70 having an expandable member 72 with an electrode layer 74 that surrounding or covering a portion of expandable member 72, and forms a sort of annular ring substantially around the circumference of the expandable member 72 portion. The electrode layer 74 is electrically coupled to a conductive cable 76 such as an insulated wire that can pass along or through probe body or shaft 78 (e.g., internal lumen) and couplable to an external power source as described above. FIG. 3B shows another embodiment of a urethral probe according to the present invention. The probe 80 includes a plurality of electrode elements 82 disposed longitudinally along the surface of an expandable member 84, with each electrode element 82 independently addressed by electrical couples 86 (e.g., conductive cables, insulated wires, or the like) passing along (e.g., embedded in the probe body) or through the probe shaft 88 and out the proximal end. Various electrode patterns and configurations can be included in probe designs according to the present invention, and probes described herein will not be limited to any particular pattern or design.

Figure 4A:
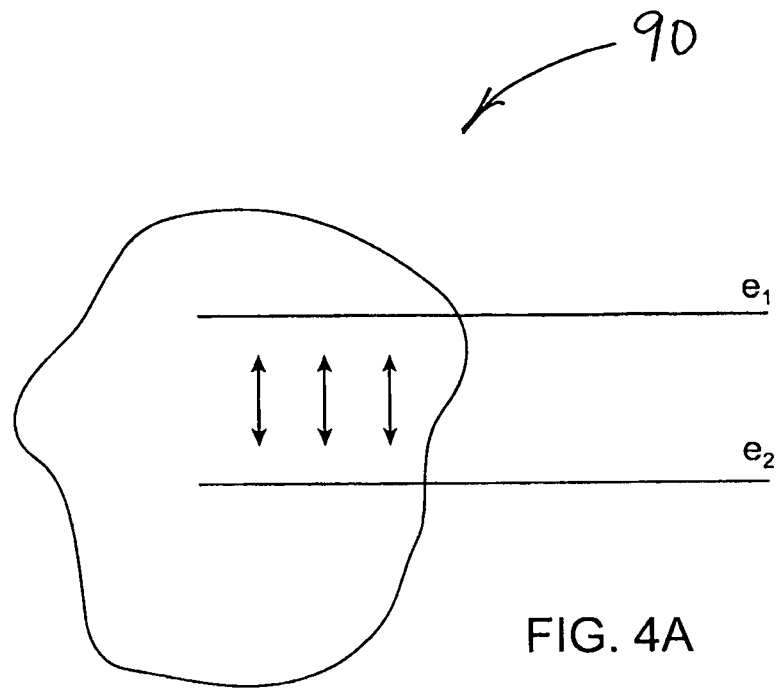
FIGS. 4A through 4C illustrate current field delivery in a target tissue according to various embodiments of the present invention.
Figure 4B:
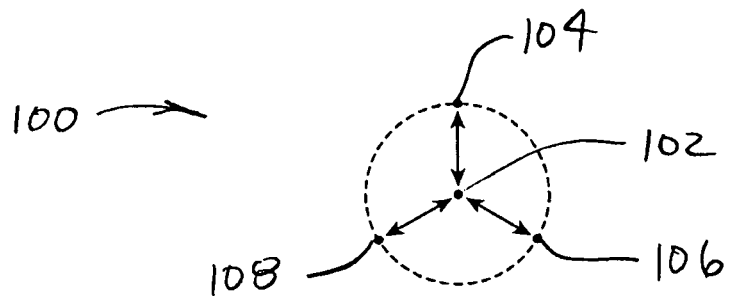
Figure 4C:
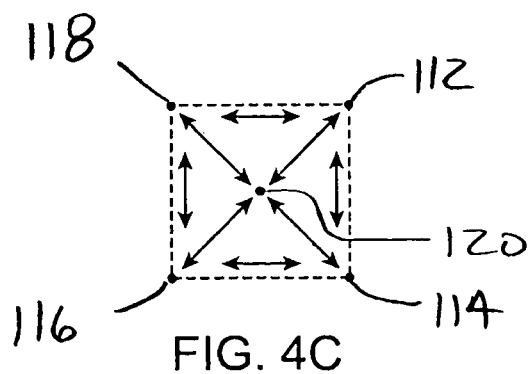

Energy delivery between positioned electrodes is further described with reference to FIGS. 4A through 4C. As described above, the present invention can include insertion and positioning of a urethral probe within a portion of the urethra passing through the patient's prostate tissue, and delivering a current field between electrode elements of a probe's expandable member and secondary electrode(s) spaced from the urethra and expandable member, and, therefore, establishing the desired current through the target tissue disposed between opposing electrodes. Electrodes can be positioned and activated in pairs or groups such that the desired electric field is delivered to the target tissue between the electrodes and, in some instances, in a radial orientation or in a plurality of different directions. FIG. 4A conceptually illustrates establishment of a current field 92 with two spaced electrode elements ($e_1$ and $e_2$) as a basic field delivery unit 90 according to an embodiment of the present invention. As shown, distal portions of two electrodes ($e_1$ and $e_2$) of a plurality positioned in a target tissue 94 and activated as an electrode pair or circuit, with the applied current substantially contained between the two. Thus, electrodes can be activated in a bipolar configuration, with current flowing between electrodes (e.g., between $e_1$ and $e_2$) and the tissue 94 between the electrodes acting as a flow medium or current pathway between the electrodes. Positioning and activation of pairs or relatively small groups of electrodes in this manner allows more precise control of the current applied to the tissue 94, containment of the applied field 92 to the desired location, as well control of heating or limited temperature increase in the target tissue 94. Several factors may lend to improved control of therapeutic effects of the delivered fields according to the present invention. First, as discussed above activating electrode in a bipolar configuration or so as to form a circuit allows the applied field to substantially be contained within the volume defined by the positioned electrodes. Second, energy delivery can be selected (e.g., frequency ranges between about 50 kHz to about 300 kHz) such that tissue heating occurs predominately due to tissue resistance, rather than the high levels of frictional heating observed at high frequencies (e.g., 500 kHz or greater). High frequency/high friction type heating is typically characterized by significant tissue temperature gradients throughout the treated tissue, with substantially higher tissue temperatures occurring near the electrode. Where high friction type heating is reduced relative to heating occurring due to tissue resistance, a more constant and controlled heating between opposing electrodes can be delivered.

In some embodiments of therapeutic energy delivery according to the present invention, electrode positioning and/or device configuration advantageously allows delivery of field throughout a target tissue volume in a plurality of different directions, such as radial field orientation and application through the target volume. FIGS. 4B and 4C illustrate simplified plan views of electrode positioning and spacing for field application according to exemplary embodiments of the present invention. As shown in FIG. 4B, a simple four electrode grouping can be selected for use in treatment, with an applied field established and current flowing between a centrally positioned electrode 102 and outer or secondary electrodes 104, 106, 108 positioned spaced from the center electrode 102. Thus, an exemplary delivery unit 100 can include a centrally located electrode 102 surrounded by spaced electrodes 104, 106, 108, with the applied field extending between the central electrode and the outer spaced electrodes. In this manner, the outer electrodes 104, 106, 108 can essentially define an ablation volume with the inner/central electrode 102 positioned within the volume. Field delivery in this way is advantageously controlled and substantially contained within the ablation volume. Furthermore, field delivery in this manner advantageously allows a current field to be established with current flow in a radial and plurality of different directions through the treatment volume, e.g., extending through or from a flow center located about the centrally positioned electrode 102. As will be recognized, the centrally positioned electrode, such as electrode 102, can include an electrode element of an expandable member of a urethral probe as described above (see, e.g., FIG. 1-2), with outer or secondary electrodes 104, 106, 108 spaced from the urethral probe and positioned in the prostate tissue of the patient. FIG. 4C illustrates exemplary electrode positioning including outer electrodes 112, 114, 116, 118 and an inner or centrally located electrode 120, for defining a discrete target tissue volume for treatment and establishing electric/treatment fields (indicated by arrows) between the electrodes, which can include a plurality of different directions or extend radially through the volume. Electrode positioning will not be limited to any particular configuration, and various arrangements will be possible.

Figure 5A:
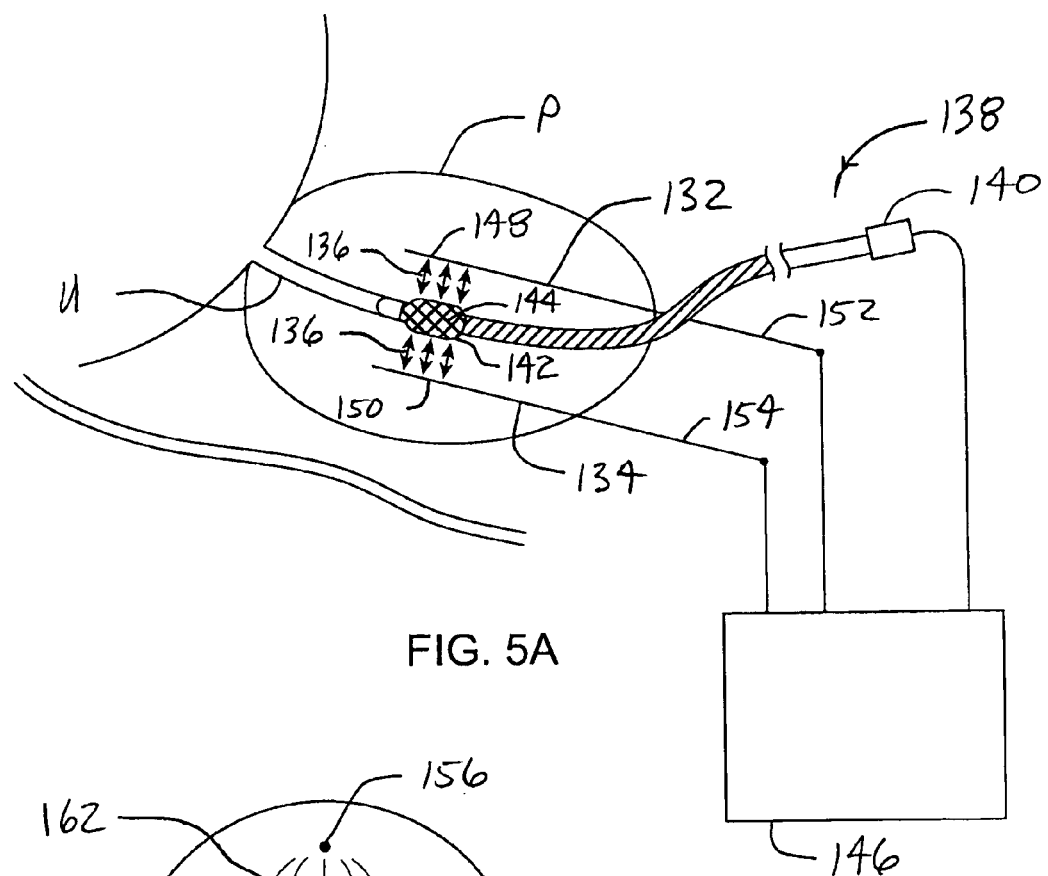
FIGS. 5A and 5B respectively illustrate a system including a transurethral probe and elongate needle electrodes, and electrode positioning in such a system, according to an embodiment of the present invention.
Figure 5B:
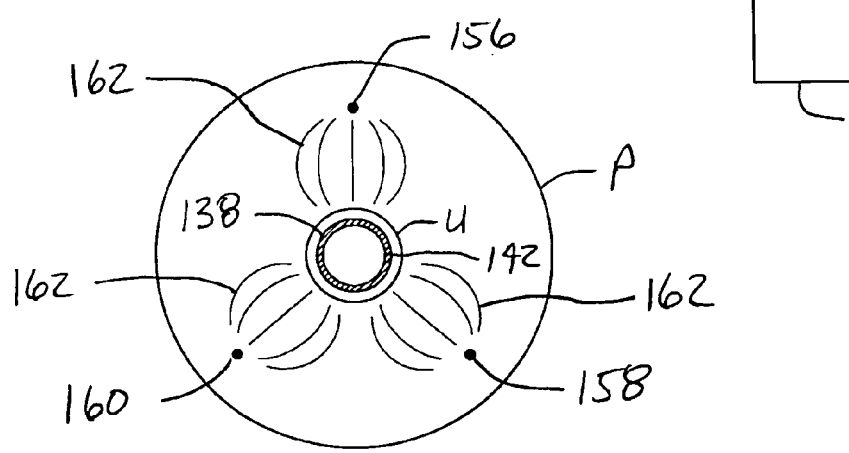

Another embodiment of the present invention is described with reference to FIGS. 5A and 5B. In this embodiment, elongate needle electrodes 132, 134 are inserted into or near the prostate tissue (P) for establishing current field 136 between the positioned needle electrodes 132, 134 and a urethral probe 138 positioned in the patient's urethra (U). A transurethral probe 138 as described above is advanced along the patient's urethra (U) and positioned in the desired location. The probe 138 includes a proximal portion 140 and a distal portion having an expandable member 142 with electrode element(s) 144 disposed thereon. The electrode element 144 of the urethral probe 138 can be coupled, e.g., about the proximal end or hub 140, to a control unit and/or power source 146. Elongate needle electrodes 132, 134 are advanced through the tissue of the patient, such as by insertion (e.g., percutaneous puncture and insertion) through the perineum of the patient and into the prostate tissue (P) or near the tissue (e.g., at the prostate tissue margin). Needle electrodes 132, 134 include a distal portion 148, 150 that will be electrically active or configured for energy delivery according to the present invention. Needle electrodes 132, 134 further include a proximal portion 152, 154 that can be positioned external the patient's body during use and manipulated for electrode positioning, and further electrically coupled to the control unit/power source 146. Needle electrodes 132, 134 may be at least partially insulated along a length so as to more precisely deliver energy or establish current at the desired location. Needle electrodes 132, 134 may be positioned and manipulated independently and/or with use of a template or guide apparatus, such as a template block having various spaced guide holes. Alternatively, two or more needles can be coupled with a housing or a cartridge-type apparatus for guided advancement and positioning. Both the urethral probe 138 and the needle electrodes 132, 134, like other components or embodiments, can be inserted and positioned under the guidance of one or more various imaging devices such as ultrasound, CT, MRI, or X-rays, including those conventionally used to monitor and assist the positioning of probes, catheters, and the like during various types of prostate treatments.

One advantage of the treatment approach as described above with reference to FIG. 5A is that needle electrodes 132, 134 can be positioned at various locations and spacings, so as to permit a wide variety of treatment configurations. In one embodiment, as illustrated in FIG. 5B, needle electrodes 156, 158, 160 can be positioned in the prostate tissue (P) and around the area of the urethra (U) where the urethra probe 138 is positioned. FIG. 5B shows a cross-sectional view of a urethra (U) with an expandable member 142 of a probe positioned therein and electrodes 156, 158, 160 positioned in the prostate tissue (P) around the urethra (U). The positioned needle electrodes 156, 158, 160, according to this embodiment, will substantially define the treatment volume, and current field 162 can be established flowing between the inner placed urethral probe electrode elements and the needle electrodes positioned 156, 158, 160 in the prostate tissue (P). Thus, current field 162 can be established flowing radially throughout the defined treatment volume around the urethra (U). The present invention is not limited to any particular electrode arrangement, and various electrode configurations and positionings can be utilized.

Figure 6A:
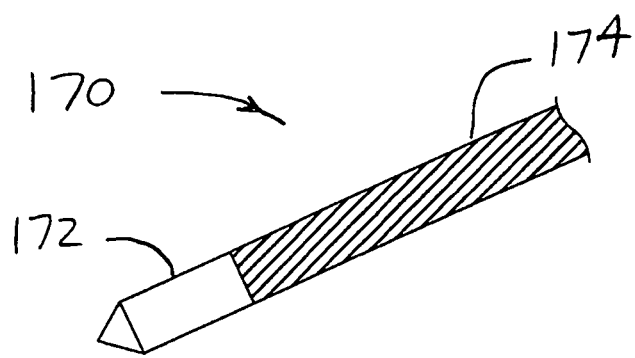
FIGS. 6A through 6C illustrate exemplary electrode embodiments, according to the present invention.
Figure 6B:
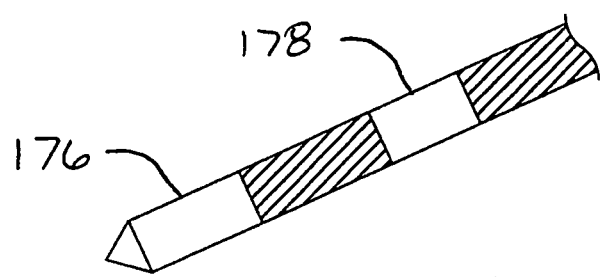
Figure 6C:
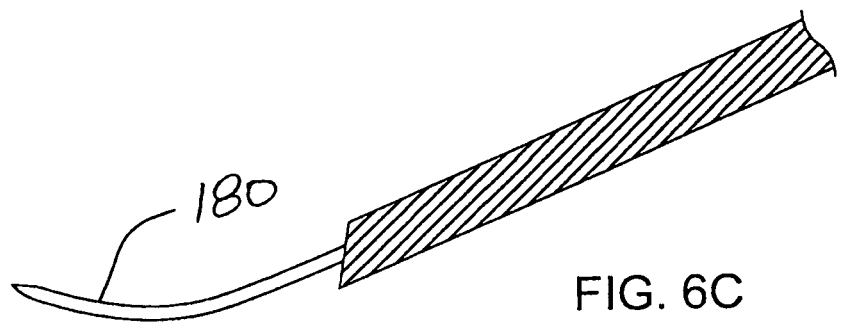

As described above, electrodes will include a substantially rigid elongate body and a distal portion having an electrically active region for delivering the desired current field to the target tissue. For tissue piercing or percutaneous access and advancement, needle electrodes will typically include a pointed or sharpened distal tip. Various electrode configurations and designs can be utilized and the current invention is not limited to any particular electrode design. Electrodes, for example, can be differentially insulated such that current delivery occurs at a non-insulated or thinly insulated region of the electrode. FIG. 6A illustrates a straight needle electrode having an electrically active region 172 and a region 174, which is non-electrically active. The needle can include an electrically conductive material (e.g., stainless steel, silver, gold, etc.) having an insulating coating on region 174 and non-insulated on the active region 172. Electrodes can include a single active region or a plurality of active regions, as shown in FIG. 6B having active regions 176, 178. In addition to more rigid straight needle type electrodes, electrodes can include a deployable element 180 that can be retractable and positioned within a lumen of a catheter-type device, as shown in FIG. 6C. The electrode element 180 can be curved (as shown) or can be substantially straight or linear. Various needle/electrode sizes and/or configurations may be utilized, and can include, without limitation, needles ranging from about 15 to about 27 gauge in size.

In another aspect, systems and methods include an elongate urethral probe, a distal expandable member with conductive electrode elements and one or more secondary electrodes deployable from a body of the elongate probe. The secondary electrodes can include an electrically conductive, shape memory metal (e.g., Nitinol) and can be deployed from the body of the elongate probes and advanced to a position spaced from the expandable member for current delivery between the deployable electrodes and the electrode elements of the expandable member. Deployable electrodes will include a proximal portion and a distal portion, with the distal portion being substantially disposed within the elongate body during non-deployed phase. The electrodes can extend through the body of the elongate probe, with the proximal portion extending out the proximal end of the elongate probe. Electrodes can be controlled/actuated from the proximal end of the probe and deployed from or retracted into the distal portion of the probe by application of force to the proximal end of the electrode.

Figure 7A:
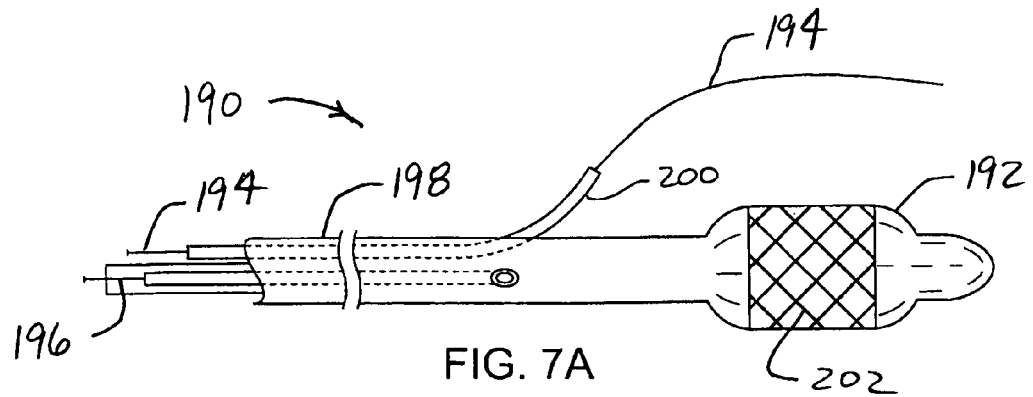
FIGS. 7A through 7C illustrate a transurethral probe having deployable secondary electrodes and probe positioning in the prostate tissue of a patient, according to an embodiment of the present invention.

A urethral probe 190 including an expandable member 192 and deployable electrode 194, 196, according to one embodiment of the present invention, is described with reference to FIG. 7A. The probe 190 includes a flexible elongate body 198 having a proximal portion and a distal portion. The distal portion includes an expandable member 192, similar to embodiments described elsewhere herein in having an expandable member, such as a balloon, with electrode elements 194, 196 disposed thereon. The body of the probe further includes a lumen with deployable electrodes 194, 196 positioned therein. Deployment of electrodes 194, 196 can include application of a force to the proximal portion of an electrode 194, 196 so as to advance the distal portion of the electrode 194, 196 from the lumen of the elongate body 198 for deployment and positioning of the electrode 194, 196. In certain embodiments, including the probe 190 illustrated in FIG. 7A, deployable electrodes 194, 196 further can optionally include a positioning microcatheter 200. The microcatheter includes an inner lumen with the smaller electrode 194 positioned therein and deployable from the microcatheter 200. Deployment of the microcatheter 200 includes application of force to the proximal portion of the microcatheter 200 and advancement of the distal portion of the microcatheter 200 from the lumen of the body for deployment and initial positioning or aiming. Deploying the microcatheter 200 from the lumen guides the microcatheter 200 along a guide path or tissue penetration path through the urethra and into the prostate tissue and can further curve in an initial desired direction or at an angle. Following deployment of the microcatheter 200, electrode 194 can be deployed from the microcatheter 200 for further positioning of the electrode 194 as illustrated in FIG. 7A. In use, the electrode 194 at least partially defines the outer portion or perimeter of the ablation volume, with the expandable member 192 positioned at about the center of the volume (e.g., current flow center), permitting current flow extending radially within the volume and between electrodes 202 of the expandable member 192 and the deployed electrode 194. While use of an aiming microcatheter 200 can advantageously facilitate improved positioning of the deployed electrode 194, probe may alternatively be designed such that electrodes deploy directly from the probe body and in the absence of an aiming microcatheter 200.

Figure 7B:
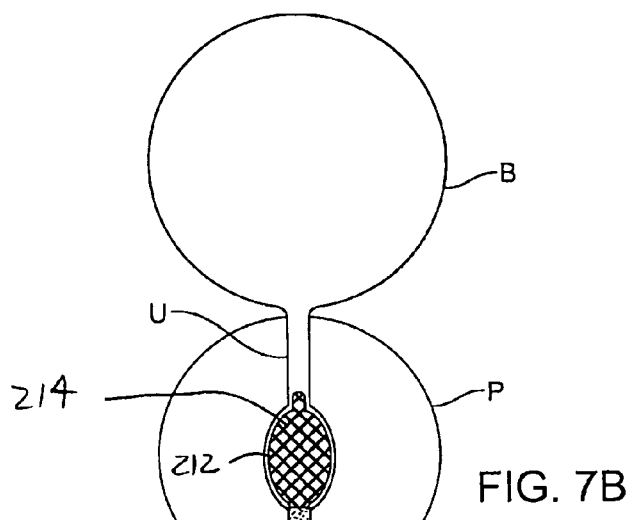
Figure 7C:
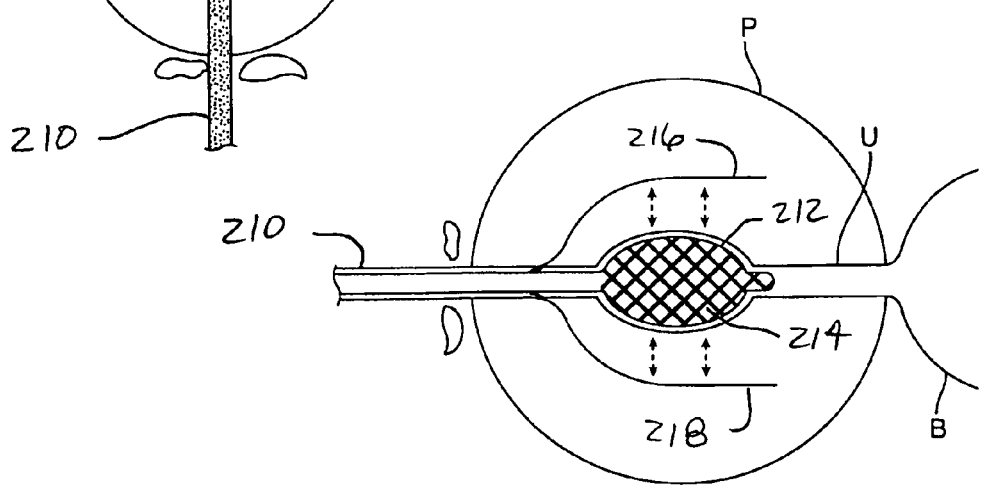

Use of a urethral probe including deployable electrodes and a distal expandable member having electrode elements, according to an embodiment of the present invention, is described with reference to FIGS. 7B and 7C. As illustrated in FIG. 7B, a distal portion of a urethral probe 210 is advanced through the patient's urethra (U) so as to position the expandable member 212 at a target location in the patient's urethra (U). The positioned expandable member 212 is inflated or expanded at the target location so as to position the conductive electrode elements 214 in better or improved contact with an inner surface of the patient's urethra (U) at the target location. As shown in FIG. 7C, the deployable electrodes 216, 218 can be advanced or deployed from the body of the probe 210 and through the urethral wall into the prostate tissue (P). As deployed, the secondary electrodes 216, 218 are spaced from the expandable member 212 positioned in the urethra (U). The deployed electrodes 216, 218 advanced or positioned in this manner can be positioned to substantially define an ablation volume with the expandable member 212 positioned within the ablation volume. Once the probe 210 is positioned as desired, and electrodes 216, 218 deployed, an electrical current flow can be established between the electrode elements 214 of the expandable member 212 and the secondary electrodes 216, 218.

In another aspect, a system of the present invention can include use of a urethral probe positioned in the urethra of the patient and a probe positioned in the rectum of the patient, with current field established between conductive electrode elements of the urethral and rectal probes, and through the tissue disposed therebetween. In such an embodiment, a urethral probe can include an elongate flexible probe as described above, including a proximal end and a distal end having an expandable member including electrode elements. The system further includes a rectal probe having a distal portion with an expandable member similar to the expandable member of the urethral probe. The rectal probe will include one or more electrode elements disposed on a surface of an expandable member. A control system including a power source is further included, the control system can be coupled to the elongate urethral probe and rectal probe and configured to provide electrical current to the electrodes so as to establish a current flow through a volume of the patient's prostate tissue and between the electrode elements of the urethral probe and electrode elements of the rectal probe.

A system 230 for establishing current flow between a urethral probe 232 and a rectal probe 234, according to the present invention is described with reference to FIGS. 8A and 8B. A urethral probe 232 is included and can include a probe as described above (see, e.g., FIGS. 1-3). The probe 232 includes a flexible elongate shaft or body, including a distal portion and a proximal portion. The distal portion includes an expandable balloon or expandable member 236 having electrode elements 238 disposed thereon, and can be expanded with the expansion of the expandable member 236 with electrode elements 238 brought into better/improved contact with the urethral wall. Similar to the urethral probe 232, the rectal probe 234 includes an elongate body with a distal portion including an expandable member 240, such as a balloon, having electrode elements 242 disposed on one or more surfaces. While conceptually similar in design, the rectal probe 234 can be sized and configured for positioning and use in a rectal cavity (R), rather than in a urethral lumen (U). Further, electrode elements 242 on the rectal probe expandable member 240 will typically be substantially confined or positioned on a side or surfaces of the expandable member 240 facing the prostate wall during energy delivery. Thus, the expandable member 240 of the rectal probe 234 need not necessarily include electrode elements spaced annularly around the expandable member 240 (though such a configuration may be utilized), but instead may include electrode elements 242 disposed on a discrete region or surface(s). The rectal probe 234, during use, is positioned in the patient's rectum (R) and upon expansion of the expandable member 240 the electrode elements 242 of the expandable member 240 are brought into improved contact with a portion of the rectal wall proximate to the prostate tissue (P).

Both the rectal probe 234 and the urethral probe 232 can be connected to an external power source and control unit for energy delivery and establishing electric current fields between the electrode elements of the urethral probe expandable member and electrode elements of the rectal probe expandable member spaced from the expandable member. Current flow established between the expandable members 236 and 240 is indicated by current flow arrows. FIG. 8B illustrates a cross-sectional view of a positioned urethral probe 232 and a positioned rectal probe 234, with current flow (indicated by field arrows) established between the expandable members 236 and 240 of the urethral probe 232 and rectal probe 234, respectively. As shown, the system can further include electrodes 246 positioned in the prostate tissue, which can include electrodes deployable from the urethral probe 232 or positioned elongate needle electrodes as described above.

Similar to described above, inflation media or fluid can be flowed into or circulated through either the urethral probe expandable member 236 or the rectal probe expandable member 240, or both. As above, fluid can be flowed at a selected temperature for heating or cooling of the tissues of the treatment areas, and/or may facilitate maintenance of the tissues at a desired treatment temperature.

Figure 9:
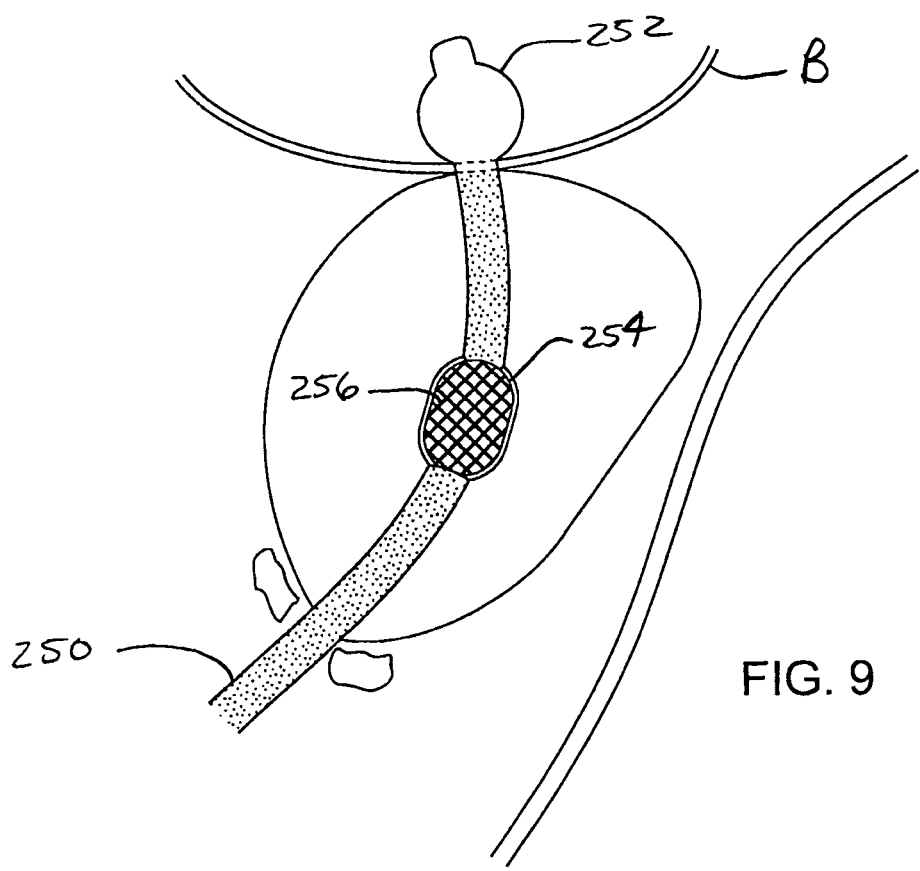
FIG. 9 illustrates a transurethral probe having a distal positioning balloon, according to an embodiment of the present invention.

As noted above, a urethral probe according to the present invention can include one or more positioning members, such as an expandable balloon, for applying a positioning force to secure positioning of the probe in the desired location. For example, while urethral probes are illustrated above as having a single expandable member, it will be understood that this and other designs/configurations of the probe may optionally further include one or more additional expandable members or balloons. For example, as illustrated in FIG. 9, a urethral probe 250 of the invention can include a Foley-type catheter design, where the probe includes a second balloon 252 located on the probe body distal to the expandable member 254 for positioning and/or anchoring in the patient's bladder (B) during use of the probe or treatment. The proximal expandable member 254 will include electrode elements 256 for energy deliver as described above.

Figure 10A:
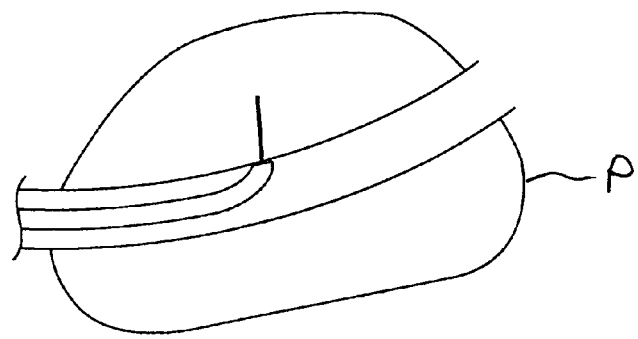
FIGS. 10A through 10D illustrates a urethral probe having deployable electrodes that can be advanced through the urethral wall and into the prostate tissue of a patient.
Figure 10B:
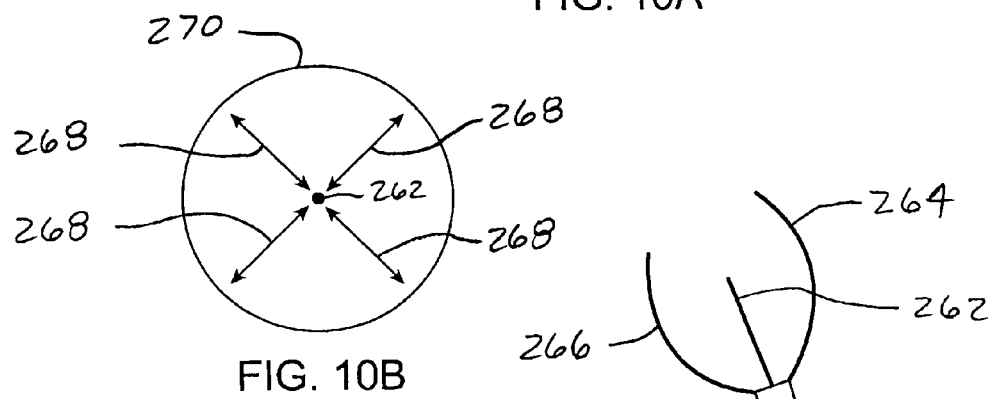
Figure 10C:
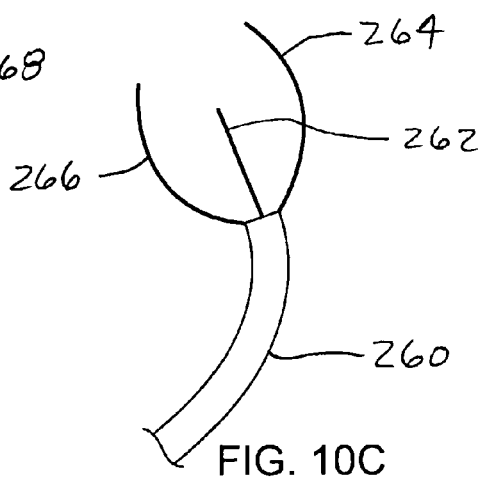

Another embodiment of the present invention is described with reference to FIGS. 10A through 10C. As illustrated, an elongate urethral probe having a plurality of deployable electrodes that can be advanced through the urethral wall and into the prostate tissue in a desired arrangement for energy delivery. An elongate urethral probe 260 can include a proximal end, a distal portion, and a plurality of electrodes 262, 264, 266 deployable from the distal portion. A method can include advancing the distal portion of the probe through the patient's urethra so as to position the distal portion near a target location in the patient's urethra. Once the distal portion is at the desired location, a plurality of outer or secondary electrodes 264, 266 can be deployed from the distal portion of the probe, through the urethral wall, and into the prostate tissue. The deployed outer or secondary electrodes 264, 266 can be positioned to substantially define an ablation volume in the prostate tissue. Further, an inner or central electrode 262 can be deployed from the distal portion of the probe 260 and through the urethral wall and into the prostate tissue (P) such that the inner/central electrode 262 is positioned within the ablation volume. Once the urethral probe 260 and needle electrodes 262, 264, 266 are positioned, treatment includes establishing an electrical current flow 268 between the inner electrode 262 and the one or more outer/secondary electrodes. FIG. 10B illustrates current flow about a flow center, between an inner or central electrode 262 and to an outer perimeter or volume 270 defined substantially by outer positioned electrodes.

Figure 10D:
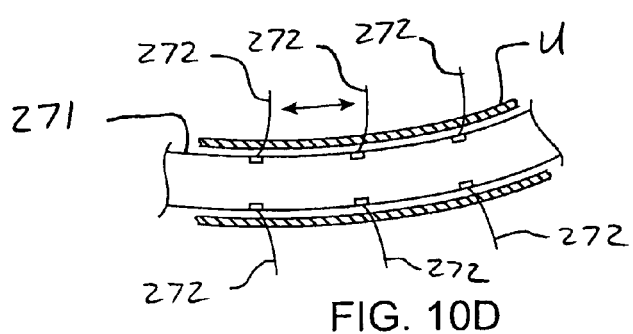

Referring to FIG. 10D, an elongate urethral probe 271 can additionally or alternatively include one or more electrodes 272 deployable from locations along the body of the probe proximal to the distal tip. Deployable electrodes can be actuated and/or controlled from the proximal end of the probe, similar to as described above. Deployment of the electrodes can include application of a force to the proximal end causing the electrodes to advance out of the probe body and through the urethral wall (U), and into the prostate tissue. Probe positioning, as shown, can include extending of the electrodes through the urethral wall in a direction perpendicular to the long axis of the probe body and into the prostate tissue. Energy application can include activation of electrodes in pairs or groups, such as differential activation in pairs to establish current flow between activated pairs, as indicated by the field arrow shown in FIG. 10D.

As mentioned above, various components of the systems described herein, including the urethral probe, rectal probe, the needle electrodes, and other components or embodiments, can be inserted and positioned under the guidance of one or more various imaging devices such as ultrasound, CT, MRI, or X-rays, including those conventionally used to monitor and assist the positioning of probes, catheters, and the like during various types of prostate treatments. Thus, probes and electrodes described herein, for example, may include in part radiopaque or radiopaque markings (e.g., tip markings) such that their positioning can be visualizable in X-ray, CT, MR or other types of imaging.

Figure 11:
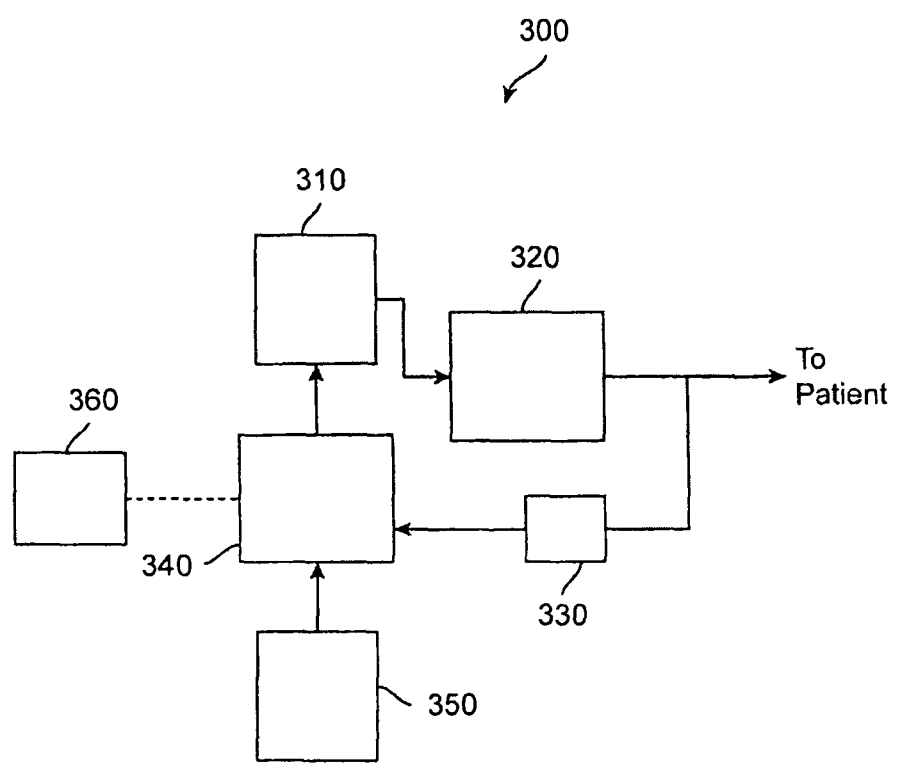
FIG. 11 includes a diagram illustrating a system according to an embodiment of the present invention.

FIG. 11 shows a block diagram illustrating a system according to an embodiment of the present invention. The system 300 can include incorporated therewith any device of the present invention for delivery of energy to the patient, and includes a power unit 310 that delivers energy to a driver unit 320 and than to electrode(s) of an inventive device. The components of the system individually or collectively, or in a combination of components, can comprise an energy source for a system of the invention. A power unit 310 can include any means of generating electrical power used for operating a device of the invention and applying electrical current to a target tissue as described herein. A power unit 310 can include, for example, one or more electrical generators, batteries (e.g., portable battery unit), and the like. Thus, in one embodiment, a system of the invention can include a portable and/or battery operated device. A feedback unit 330 measures electric field delivery parameters and/or characteristics of the tissue of the target tissue region, measured parameters/characteristics including without limitation current, voltage, impedance, temperature, pH and the like. One or more sensors (e.g., temperature sensor, impedance sensor, thermocouple, etc.) can be included in the system and can be coupled with the device or system and/or separately positioned at or within the patient's tissue. These sensors and/or the feedback unit 330 can be used to monitor or control the delivery of energy to the tissue. The power unit 310 and/or other components of the system can be driven by a control unit 340, which may be coupled with a user interface 350 for input and/or control, for example, from a technician or physician. The control unit 340 and system 300 can be coupled with an imaging system 360 (see above) for locating and/or characterizing the target tissue region and/or location or positioning the device during use.

A control unit can include a, e.g., a computer or a wide variety of proprietary or commercially available computers or systems having one or more processing structures, a personal computer, and the like, with such systems often comprising data processing hardware and/or software configured to implement any one (or combination of) the method steps described herein. Any software will typically include machine readable code of programming instructions embodied in a tangible media such as a memory, a digital or optical recovering media, optical, electrical, or wireless telemetry signals, or the like, and one or more of these structures may also be used to transmit data and information between components of the system in any wide variety of distributed or centralized signal processing architectures.

Components of the system, including the controller, can be used to control the amount of power or electrical energy delivered to the target tissue. Energy may be delivered in a programmed or pre-determined amount or may begin as an initial setting with modifications to the electric field being made during the energy delivery and ablation process. In one embodiment, for example, the system can deliver energy in a "scanning mode", where electric field parameters, such as applied voltage and frequency, include delivery across a pre-determined range. Feedback mechanisms can be used to monitor the electric field delivery in scanning mode and select from the delivery range parameters optimal for ablation of the tissue being targeted.

Systems and devices of the present invention can, though not necessarily, be used in conjunction with other systems, ablation systems, cancer treatment systems, such as drug delivery, local or systemic delivery, surgery, radiology or nuclear medicine systems (e.g., radiation therapy), and the like. Another advantage of the present invention, is that treatment does not preclude follow-up treatment with other approaches, including conventional approaches such as surgery and radiation therapy. In some cases, treatment according to the present invention can occur in conjunction or combination with therapies such as chemotherapy. Similarly, devices can be modified to incorporate components and/or aspects of other systems, such as drug delivery systems, including drug delivery needles, electrodes, etc.

It is understood that the examples and embodiments described herein are for illustrative purposes only and that various modifications or changes in light thereof will be suggested to persons skilled in the art and are to be included within the spirit and purview of this application and scope of the appended claims. Numerous different combinations are possible, and such combinations are considered part of the present invention.

What is claimed is:

1. A method of delivering an electric field to destroy cancerous cells of a prostate tissue of a patient including positioning of an elongate urethral probe comprising a proximal end and a distal portion having an expandable member, and one or more conductive electrode elements disposed on an outer surface of the expandable member, the method comprising:

advancing the distal portion of the probe through the patient's urethra so as to position the expandable member at a target location in the patient's urethra;

expanding the expandable member at the target location so as to position the conductive electrode elements in contact with an inner surface of the patient's urethra at the target location;

positioning one or more secondary electrodes such that a current transfer region of each of the one or more secondary electrodes is disposed within or adjacent to the prostate tissue and spaced from the electrode elements of the expandable member, thereby at least partially defining a treatment volume; and establishing an alternating electrical current flow between the electrode elements of the expandable member and the one or more secondary electrodes by delivering electrical current from at least one of (a) at least one of the one or more conductive electrode elements and (b) at least one of the one or more current transfer regions, and through tissue of the treatment volume, so as to preferentially destroy cancerous cells of the prostate tissue in the treatment volume relative to non-cancerous cells in the treatment volume.

2. The method of claim 1, wherein electrical current flow is established so as to heat the target tissue to an average temperature of less than about 50 degrees C.

3. The method of claim 1, the alternating current flow comprising a frequency of less than about 300 kHz.

4. The method of claim 3, the alternating electrical current flow comprising a frequency from about 50 kHz to about 250 kHz.

5. The method of claim 3, the alternating electrical current flow comprising a frequency of about 100 kHz.

6. The method of claim 1, wherein the elongate urethral probe comprises one or more secondary electrodes deployable from a body of the elongate probe.

7. The method of claim 6, further comprising deploying one or more secondary electrodes from the body of the probe and through the urethral wall into the prostate tissue and spaced from the positioned expandable member, the deployed electrodes substantially defining an ablation volume with the expandable member positioned within the ablation volume; and establishing an electrical current flow between the electrode elements of the expandable member and the one or more secondary electrodes so as to preferentially destroy cancerous cells of the prostate tissue.

8. The method of claim 1, wherein the secondary electrodes comprise elongate needle electrodes advanced through the perineum of the patient and into the prostate tissue.

9. The method of claim 8, further comprising establishing an electrical current flow between the electrode elements of the expandable member and the positioned needle.

10. The method of claim 1, wherein establishing the current flow comprises applying an electrical through a treatment volume so as to provide an electric field extending radially outward from a current flow center.

11. The method of claim 1, further comprising flowing a heated or cooled inflation media through the expandable member during energy delivery.

12. The method of claim 1, wherein the method comprises treatment of benign prostate hyperplasia (BPH).

13. A method of delivering an electric field to destroy cancerous cells of a prostate tissue of a patient including positioning of an elongate urethral probe comprising a proximal end and a distal portion having an expandable member, the expandable member comprising one or more conductive electrode elements, the method comprising:
  advancing the distal portion of the probe through the patient's urethra to position the expandable member of the urethral probe at a target location in the patient's urethra;
  expanding the expandable member of the urethral probe at the target location so as to position the conductive electrode elements in contact with an inner surface of the patient's urethra at the target location;
  positioning a second probe in a rectal cavity of the patient, the second probe comprising one or more conductive electrode elements disposed on a surface of an expandable member, the second probe positioned such that the conductive electrode elements of the expandable member contact an inner surface of the patient's rectal wall near the prostate; and
  establishing an alternating electrical current flow between the conductive electrode elements of the urethral probe and the conductive electrode elements of the second probe by delivering electrical current from at least one of (a) at least one of the one or more conductive elements of the urethral probe and (b) at least one of the one or more conductive elements of the second probe so as to preferentially destroy cancerous cells of the prostate tissue relative to non-cancerous cells of the tissue disposed between the urethral probe expandable member and the second probe expandable member.

14. The method of claim 13, wherein electrical current flow is established so as to heat the target tissue to an average temperature of 40 degrees C. to 48 degrees C.

15. The method of claim 14, the electrical current flow comprising a frequency of about 50 kHz to about 300 kHz.

16. The method of claim 15, the alternating electrical current flow comprising a frequency of about 100 kHz.

17. The method of claim 13, further comprising flowing a heated or cooled inflation media through the expandable member of the urethral probe, the rectal probe, or both, during energy delivery.

18. A method of delivering an electric field to destroy cancerous cells or hyperplastic cells of a prostate tissue of a patient including positioning of an elongate urethral probe comprising a proximal end and a distal portion having one or more conductive electrode elements deployable therefrom, the method comprising:
  advancing the distal portion of the probe through the patient's urethra to position the distal portion of the urethral probe at a target location in the patient's urethra;
  deploying one or more electrodes from the distal portion of the probe so as to penetrate through the urethral wall and into the prostate tissue such that a current transfer region of each of the deployed electrodes is spaced laterally from the urethral probe distal portion so as to at least partially define a treatment volume; and
  establishing an alternating electrical current flow between the deployed electrode elements of the urethral probe by delivering electrical current from at least one of the one or more current transfer regions so as to preferentially destroy cancerous cells of the prostate tissue of the treatment volume disposed between the electrodes relative to non-cancerous cells of the treatment volume.

19. The method of claim 18, wherein the alternating electrical current flow comprises a frequency of about 50 kHz to about 300 kHz.

20. A method of delivering an electric field to destroy cancerous cells of a target tissue of a patient including positioning of an elongate probe in a body lumen of the patient, the probe comprising a proximal end and a distal portion having an expandable member, and one or more conductive electrode elements disposed on an outer surface of the expandable member, the method comprising:
  advancing the distal portion of the probe through the patient's body lumen so as to position the expandable member at a target location in the lumen;
  expanding the expandable member at the target location so as to position the conductive electrode elements in contact with an inner surface of the patient's lumen at the target location;
  positioning one or more secondary electrodes such that a current transfer region of each of the one or more secondary electrodes is disposed within or adjacent to the target tissue and spaced laterally from the electrode elements of the expandable member so as to at least partially define a treatment volume; and
  establishing an alternating electrical current flow between the electrode elements of the expandable member and the one or more secondary electrodes by delivering electrical current from at least one of (a) at least one of the one or more conductive electrode elements and (b) at least one of the one or more current transfer regions so as to preferentially destroy cancerous cells of the target tissue within the treatment volume relative to non-cancerous cells within the treatment volume.

21. The method of claim 20, wherein the alternating electrical current flow comprises a frequency of about 50 kHz to about 300 kHz.

* * * * *